United States Patent
Grambichler et al.

(10) Patent No.: US 9,939,410 B2
(45) Date of Patent: Apr. 10, 2018

(54) TRANSMISSION OF INFORMATION ASSOCIATED WITH A POSSIBLE SENSOR FAULT OF A MAGNETIC SENSOR

(71) Applicant: Infineon Technologies AG, Neubiberg (DE)

(72) Inventors: Klaus Grambichler, Velden (AT); Michael Burk Westpfahl, Tegernsee (DE)

(73) Assignee: Infineon Technologies AG, Neubiberg (DE)

( * ) Notice: Subject to any disclaimer, the term of this patent is extended or adjusted under 35 U.S.C. 154(b) by 227 days.

(21) Appl. No.: 14/842,064

(22) Filed: Sep. 1, 2015

(65) Prior Publication Data

US 2017/0059526 A1   Mar. 2, 2017

(51) Int. Cl.
*G01M 15/06* (2006.01)
*G01N 27/82* (2006.01)
*G01D 5/20* (2006.01)
*G01R 35/00* (2006.01)

(52) U.S. Cl.
CPC ............. *G01N 27/82* (2013.01); *G01D 5/20* (2013.01); *G01M 15/06* (2013.01); *G01R 35/00* (2013.01)

(58) Field of Classification Search
USPC ............... 73/114.02, 114.03, 114.04, 114.26, 73/114.27, 114.28
See application file for complete search history.

(56) References Cited

U.S. PATENT DOCUMENTS

| | | | | |
|---|---|---|---|---|
| 7,408,452 B2 * | 8/2008 | Knittl | ............... | B60G 17/01933 180/197 |
| 7,772,837 B2 * | 8/2010 | Kassner | ............... | G01D 5/2457 324/207.25 |
| 2007/0256482 A1 * | 11/2007 | Sheikh | ................... | G01M 15/06 73/114.26 |
| 2009/0326860 A1 * | 12/2009 | Hainz | ................ | G01D 5/24452 702/163 |
| 2010/0107747 A1 * | 5/2010 | Rolew | ................... | F02D 41/009 73/114.26 |
| 2017/0092024 A1 * | 3/2017 | Slama | .................. | G07C 5/0816 |

* cited by examiner

*Primary Examiner* — Eric S McCall
(74) *Attorney, Agent, or Firm* — Harrity & Harrity, LLP

(57) ABSTRACT

A magnetic sensor may sense a magnetic field during a rotation of a wheel. The sensed magnetic field may represent a profile of the wheel during the rotation. The magnetic sensor may determine, based on the sensed magnetic field, information associated with a possible fault of at least one of the magnetic sensor or the wheel. The magnetic sensor may transmit a first set of output pulses corresponding to the profile of the wheel during the rotation. The first set of output pulses may be transmitted during the rotation of the wheel. The magnetic sensor may transmit a second set of output pulses that corresponds to the information associated with the possible fault.

20 Claims, 13 Drawing Sheets

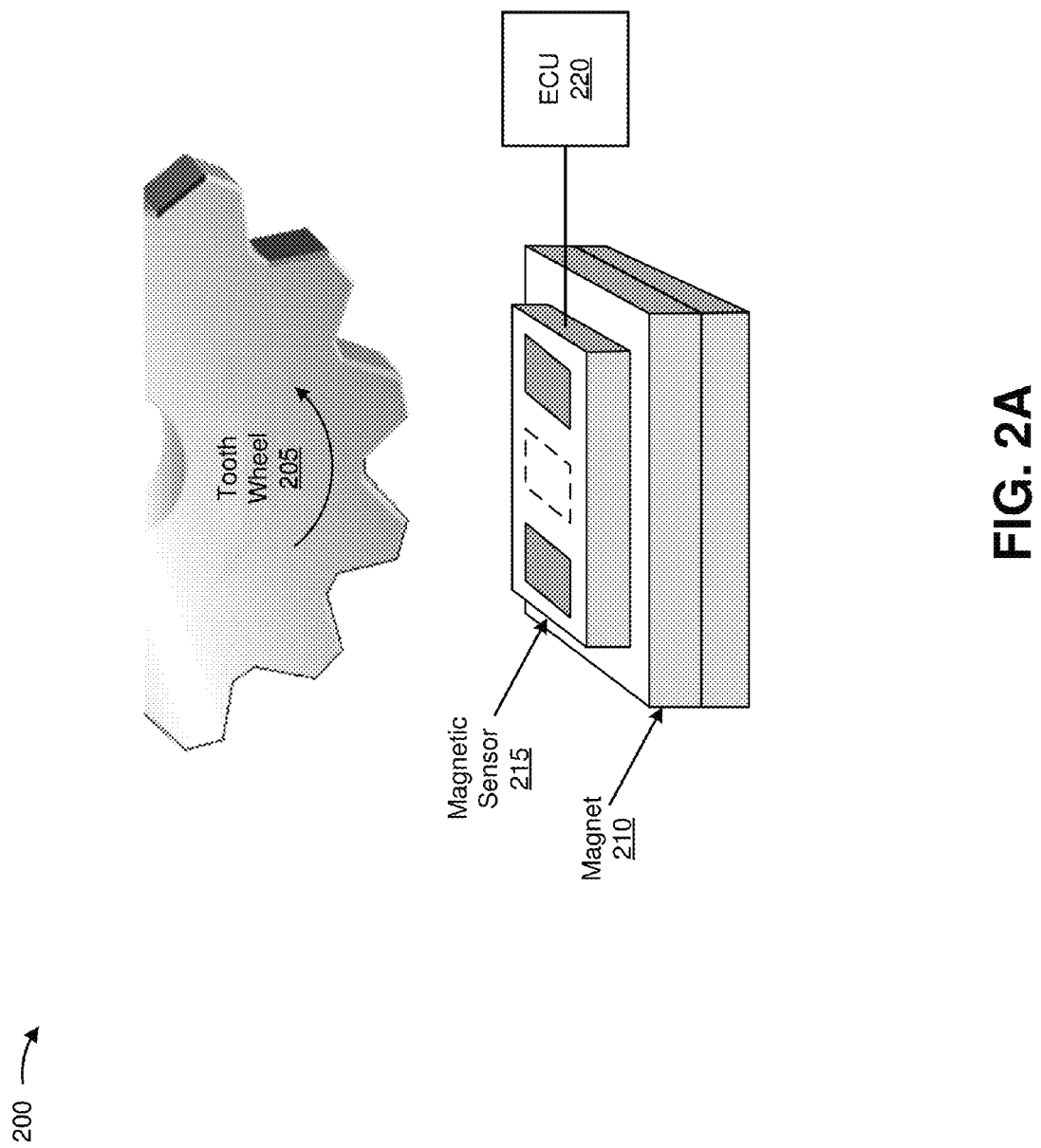

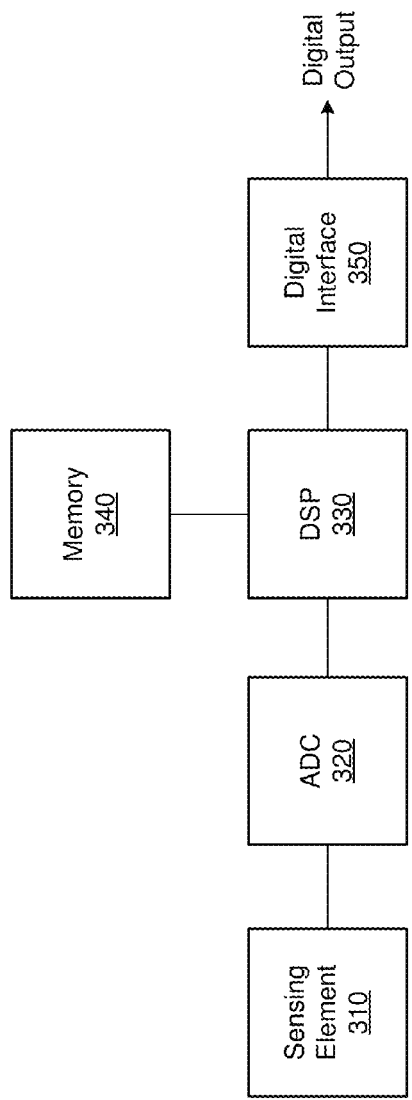

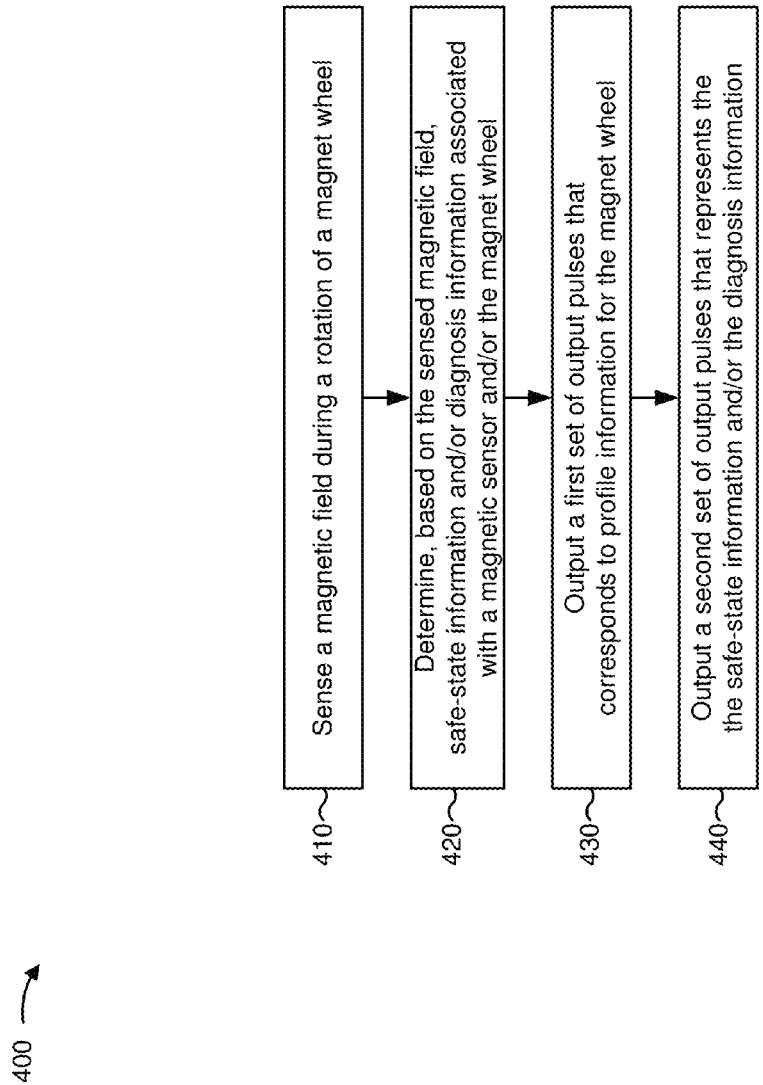

TRANSMISSION OF INFORMATION ASSOCIATED WITH A POSSIBLE SENSOR FAULT OF A MAGNETIC SENSOR

BACKGROUND

A magnetic sensor may sense a magnetic field produced or distorted by a rotating magnet wheel. The magnetic sensor may output, based on the sensed magnetic field, a signal for use in identifying a position of the magnet wheel, a rotational speed of the magnet wheel, or the like.

SUMMARY

According to some possible implementations, a magnetic sensor may include one or more components configured to: sense a magnetic field during a rotation of a wheel, where the sensed magnetic field may represent a profile of the wheel during the rotation; determine, based on the sensed magnetic field, information associated with a possible fault of at least one of the magnetic sensor or the wheel; transmit a first set of output pulses corresponding to the profile of the wheel during the rotation, where the first set of output pulses may be transmitted during the rotation of the wheel; and transmit a second set of output pulses that corresponds to the information associated with the possible fault.

According to some possible implementations, a magnetic sensor may include one or more sensor components configured to: sense, during a rotation of a wheel, a magnetic field that corresponds to profile information associated with the wheel; determine, based on the sensed magnetic field, information associated with an operational state of at least one of the magnetic sensor or the wheel; output, during the rotation of the magnet wheel, a first set of output pulses that represents the profile information associated with the magnet wheel; and output a second set of output pulses that represents the information associated with the operational state.

According to some possible implementations, a method may include sensing, by a magnetic sensor, a magnetic field during a rotation of a wheel, where the sensed magnetic field may correspond to a profile of the wheel during the rotation; determining, by the magnetic sensor and based on the sensed magnetic field information associated with a possible fault of the magnetic sensor or the wheel; providing, by the magnetic sensor and during the rotation of the wheel, a first set of output pulses associated with the profile of the wheel; and providing, by the magnetic sensor, a second set of output pulses associated with the information associated with the possible fault of the magnetic sensor or the wheel.

BRIEF DESCRIPTION OF THE DRAWINGS

FIGS. 2A and 2B are diagrams of example environments in which apparatuses described herein may be implemented;

FIG. 3 is a diagram of example components of a magnetic sensor included in the example environment of FIGS. 2A and 2B;

FIG. 4 is a flow chart of an example process for transmitting a set of output pulses that corresponds to safe-state information and/or diagnosis information associated with a magnetic sensor and/or a magnet wheel;

DETAILED DESCRIPTION

Figure 1A:
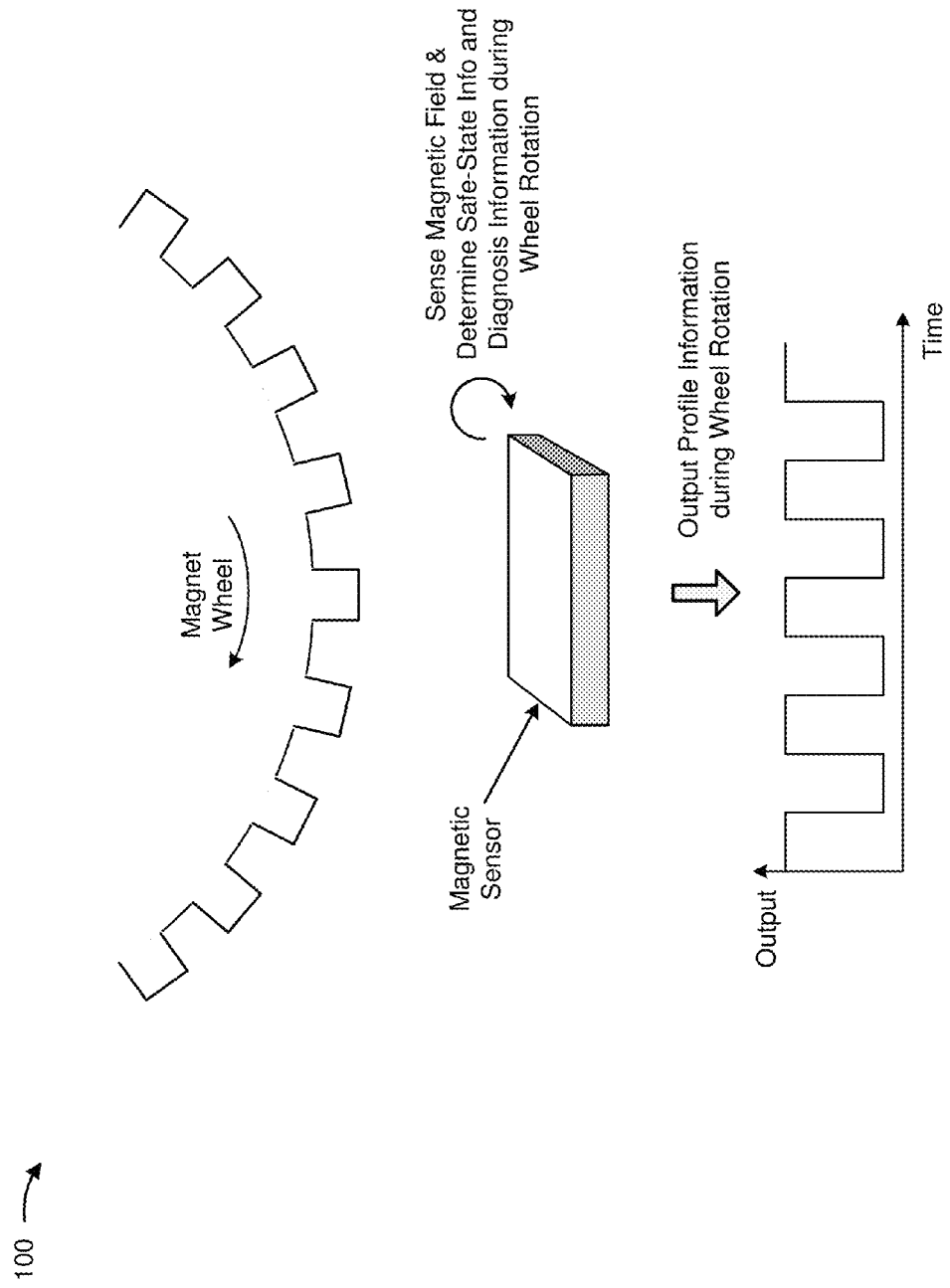
FIGS. 1A and 1B are diagrams of an overview of an example implementation described herein.

The following detailed description of example implementations refers to the accompanying drawings. The same reference numbers in different drawings may identify the same or similar elements.

A magnetic sensor may transmit, via a transmission interface (e.g., a voltage interface, a current interface, etc.) of an output terminal, profile information for a magnet wheel associated with a rotating object, such as a crankshaft of a motor vehicle, a camshaft of a motor vehicle, or the like. The profile information may correspond to a rotational position of the magnet wheel during the rotation. For example, a magnetic sensor may transmit profile information for a tooth wheel, attached to a crankshaft, where each tooth may distort a magnetic field sensed by the magnetic sensor. Here, the magnetic sensor may modify a signal (e.g., a voltage signal, a current signal, etc.), provided via a transmission interface of the output terminal, by transmitting a pulse (e.g., a voltage pulse, a current pulse, etc.) that corresponds to each tooth of the tooth wheel.

In some implementations, the magnetic sensor may also modify the signal to indicate a direction of the rotation of the magnet wheel. For example, the magnetic sensor may transmit a voltage pulse with a first pulse length (e.g., 45 microseconds (μs)) when the magnet wheel is rotating in a first direction (e.g., a forward direction) and may output a voltage pulse with a second pulse length (e.g., 90 μs, 135 μs, etc.) when the magnet wheel is rotating in a second direction (e.g., a rearward direction). In some cases, the magnet wheel may include a quantity of teeth at particular intervals, such as 60 teeth at every six degrees around a circumference of the tooth wheel. In some cases, the magnet wheel may include a quantity of teeth of varying length and/or a quantity of tooth gaps of varying length. Alternatively, the magnet wheel may be an encoder wheel that includes a quantity of alternating poles.

In some cases, one or more teeth of the tooth wheel may not be formed (e.g., tooth 59 and tooth 60) in order to create a reference zone gap that is wider than a tooth gap width (e.g., a width between two formed teeth). The reference zone gap may allow an electronic control unit (ECU), that receives the signal transmitted by the magnetic sensor, to identify (e.g., based on detecting the reference zone gap in the signal) a tooth that immediately follows the reference zone gap (e.g., tooth 1) that corresponds to a defined angle (e.g., zero degrees). The ECU may then calibrate the rotating part (e.g., a crankshaft, a camshaft, etc.) based on detecting that the tooth wheel is at the defined angle. Here, each subsequent pulse in the received signal may indicate an increase in the angle of the rotating part by a particular amount (e.g., six degrees when the tooth wheel includes 58 teeth and a two-tooth reference zone gap). In some implementations, such as in the case of a crankshaft, the falling edge of a signal may be used to transmit the profile information associated with the tooth wheel. In some implementations, such as in the case of a camshaft, the rising edge and the falling edge of a signal may be used to transmit the profile information associated with the tooth wheel.

However, in the automotive context, functional safety standards may indicate that the magnetic sensor should also be capable of signaling a possible fault, associated with the magnetic sensor and/or the tooth wheel, to the ECU. For example, for a system including a crankshaft sensor, a camshaft sensor, and an ECU, ISO 26262 indicates that the crankshaft sensor and/or the camshaft sensor should be capable of independently signaling a possible sensor fault and/or an operational state in order to achieve high safety levels for any type of fail safe or fail operation automotive systems (e.g., rather than the ECU detecting the possible fault based on comparing signals transmitted by both the crankshaft sensor and the camshaft sensor and/or another sensor, such as a transmission sensor). In such a case, it follows that the magnetic sensor may need to be capable of transmitting information associated with a possible fault of the magnetic sensor, such as safe-state information, diagnosis information, or the like.

Implementations described herein may allow a magnetic sensor to transmit safe-state information and/or diagnosis information, associated with a possible fault, without compromising an ability of the magnetic sensor to transmit profile information associated with a magnet wheel. For example, implementations described herein may allow the magnetic sensor to transmit the safe-state information and/or the diagnosis information by transmitting one or more voltage pulses (e.g., during a time period corresponding to a reference zone associated with the magnet wheel, during time periods corresponding to one or more tooth gaps associated with the magnet wheel, at another time during the rotation of the magnet wheel, etc.) and/or by outputting one or more current pulses during the rotation of the magnet wheel.

Notably, while processes and/or methods described herein are described in the context of a magnetic sensor associated with a tooth wheel and a magnet (e.g., a backbias magnet included in the magnetic sensor), these processes and/or methods may also apply to other contexts, such as in the context of a magnetic field produced by a encoder wheel and sensed by the magnetic sensor, in the context of another physical measurement principle, such as an optical system that uses a laser beam deflected by the tooth wheel, or the like. In other words, implementations described herein may apply to other contexts that use features of a wheel (e.g., a tooth wheel, an encoder wheel, etc.) to encode position information and/or speed information (i.e., independent of the measurement principle).

Figure 1B:
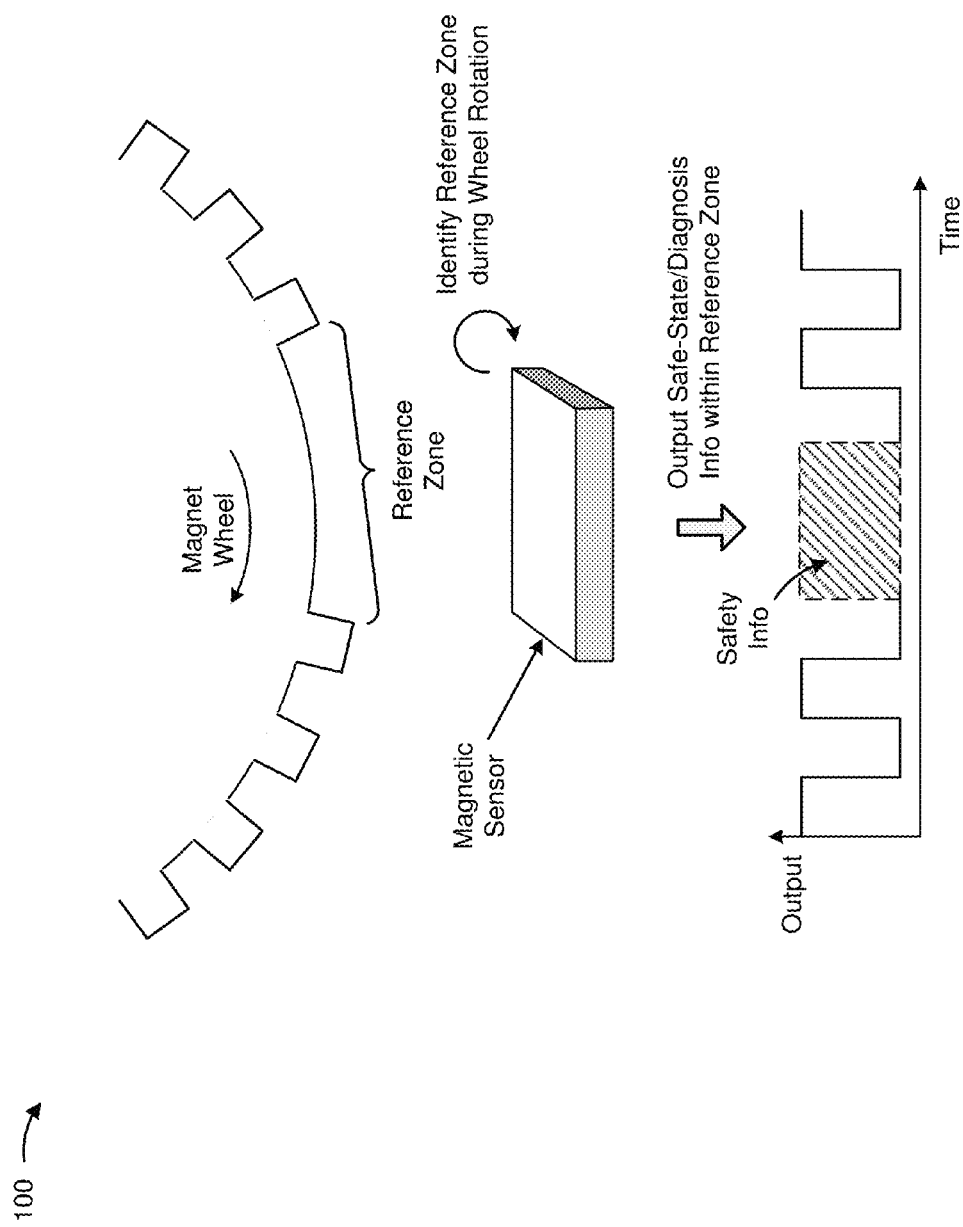

FIGS. 1A and 1B are diagrams of an overview of an example implementation 100 described herein. For the purposes of FIG. 1A, a magnetic sensor is positioned to sense a magnetic field associated with a magnet wheel, and the magnet wheel includes a set of teeth on a first section of a circumference of the magnet wheel and a reference zone gap (e.g., a section without any teeth) on a second section of the circumference of the magnet wheel. Further, assume that the magnetic sensor is configured to provide, to an ECU and during a rotation of the wheel, a signal that represents profile information of the magnet wheel (e.g., a signal that identifies each tooth as detected by the magnetic sensor).

As shown in FIG. 1A, the magnet wheel may rotate in a particular direction, and the magnetic sensor may sense a magnetic field (e.g., produced by a magnet of the magnetic sensor and distorted by the teeth of the magnet wheel during the rotation). As shown, the magnetic sensor may determine, based on the magnetic field sensed during the rotation of the magnet wheel, safe-state information and/or diagnosis information. The safe-state information may include information indicating that the magnetic sensor has detected a potential problem while continuing to transmit the profile information. The diagnosis information may include information that identifies a cause for a potential problem detected by the magnetic sensor. The diagnosis information may also include sensor status information (e.g., temperature, measured magnetic field strength/flux value, etc.) which may be relevant to an overall system or indicate a system issue, but may not indicate a problem or failure associated with the magnetic sensor.

As further shown in FIG. 1A, the magnetic sensor may transmit (e.g., in real-time, in near real-time), during the rotation of the magnet wheel associated with the first section of the circumference, a signal that represents the profile information associated with the magnet wheel. For example, as shown, the magnetic sensor may modify a signal by outputting a pulse of a particular duration (e.g., 45 µs, 90 µs, etc.) associated with each tooth of the magnet wheel (e.g., where each falling edge of the signal may identify an end of a tooth).

As shown in FIG. 1B, the magnetic sensor may identify the reference zone gap associated with the second section of the circumference (e.g., by detecting a longer gap between two of the teeth during the rotation of the magnet wheel). As further shown, within a time period corresponding to the reference zone gap of the magnet wheel (e.g., during the same rotation of the wheel, during a subsequent rotation of the wheel), the magnetic sensor may modify the signal to transmit the safe-state information and/or the diagnosis information by transmitting one or more pulses during a time period associated with the reference zone gap. In this example, the ECU may be configured to receive the pulse transmitted during the time period associated with the reference zone gap, and may determine the safe-state information and/or the diagnosis information based on a pulse length of the reference zone gap pulse (e.g., by interpreting the pulse length as a sequence of bits based on information stored by the ECU).

In this way, a magnetic sensor may transmit safe-state information and/or diagnosis information, associated with a possible magnetic sensor fault, without compromising an ability of the magnetic sensor to transmit profile information associated with a magnet wheel. While example implementation 100 is described in the context of outputting the pulses during a time period corresponding to the reference zone gap, in some implementations, the magnetic sensor may transmit the safe-state information and/or the diagnosis information at another time, such as during time periods corresponding to one or more tooth gaps associated with the magnet wheel, or at another time during the rotation of the magnet wheel, as described below.

Figure 2B:
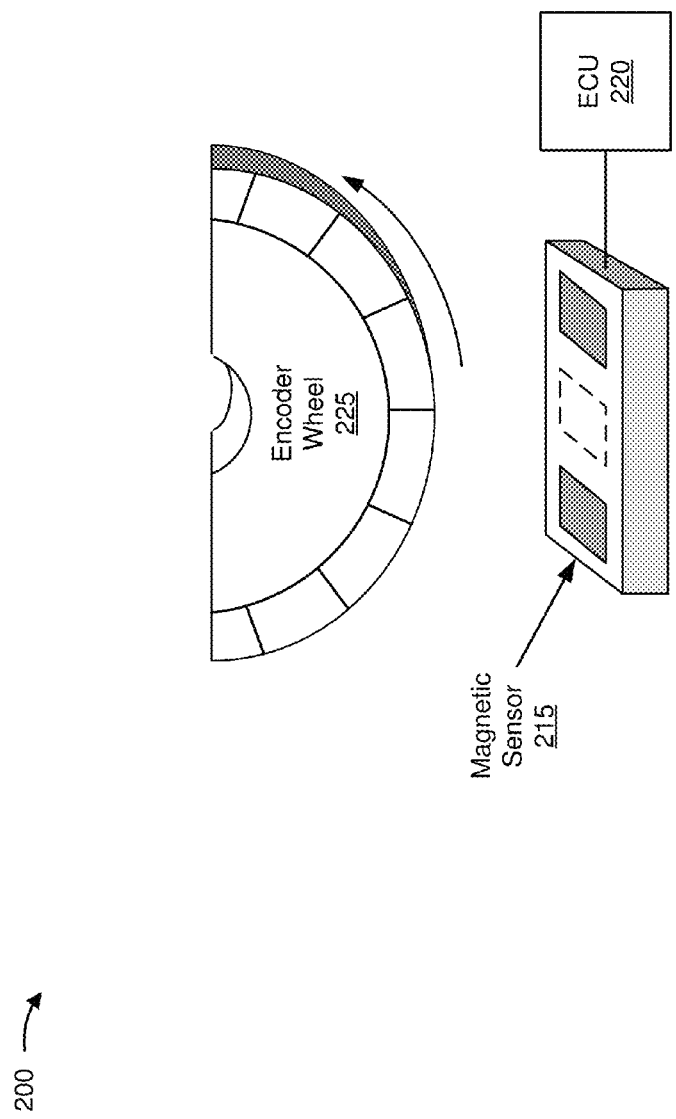

FIGS. 2A and 2B are diagrams of example environments 200 in which apparatuses described herein may be implemented. As shown in FIG. 2A, environment 200 may include a tooth wheel 205, a magnetic sensor 215, a magnet 210, and an ECU 220.

Tooth wheel 205 may include a wheel comprising a set of teeth. In some implementations, tooth wheel 205 may, during a rotation, distort a magnetic field of a magnet 210 such that magnetic sensor 215 may sense the distorted magnetic field associated with magnet 210. In some implementations, tooth wheel 205 may be comprised of a ferromagnetic material, and may produce a magnetic field. In some implementations, tooth wheel 205 may be attached to or coupled with an object for which a speed, a rotational direction, and/or a position is to be measured, such as a cylindrical structure (e.g., a crankshaft, a camshaft, a rotating cylinder, etc.), a wheel structure (e.g., associated with a tire), an axle (e.g., a vehicle axle), or the like.

In some implementations, tooth wheel 205 may include a first section that includes a set of teeth around a first portion of a circumference of tooth wheel 205, and a second section that has no teeth around a second portion of the circumference of tooth wheel 205. Within the first section, each of the set of teeth may be separated by a particular width (herein referred to as a tooth gap), and the second section may have a width that is greater than one tooth gap (herein referred to as a reference zone gap). In some implementations, such as in a crankshaft context, tooth wheel 205 may include a symmetrical tooth wheel, where teeth of tooth wheel 205 have a same width and tooth gaps of tooth wheel 205 have a same width (other than within the reference zone). In some implementations, such as in a camshaft context, tooth wheel 205 may include an asymmetrical tooth wheel, where teeth of tooth wheel 205 have varying widths and/or tooth gaps of tooth wheel 205 have varying widths (e.g., with no reference zone).

Magnet 210 may include a magnet that produces a magnetic field that may be sensed by magnetic sensor 215. In some implementations, magnet 210 may be positioned such that the magnetic field, produced by magnet 210, is distorted by tooth wheel 205. Additionally, or alternatively, magnet 210 may include a backbias magnet and/or may be positioned near, included in, and/or attached to magnetic sensor 215.

Magnetic sensor 215 may include a housing associated with one or more components of a sensor, such as a magnetoresistive (MR) sensor, a Hall effect sensor, a variable reluctance sensor (VRS), a fluxgate sensor, or the like. In some implementations, magnetic sensor 215 may be connected to ECU 220 such that magnetic sensor 215 may transmit profile information, safe-state information, and/or diagnosis information to ECU 220 via one or more transmission interfaces (e.g., a voltage interface, a current interface, etc.) and/or via one or more output terminals. In some implementations, magnetic sensor 215 may include a three-wire sensor (e.g., including one output terminal), a four-wire sensor (e.g., including two output terminals), or the like. Additional details regarding magnetic sensor 215 are described below with regard to FIG. 3.

ECU 220 may include a device associated with controlling one or more electrical systems and/or electrical subsystems, for example, one or more electrical systems and/or one electrical subsystems included in a motor vehicle. For example, ECU 220 may include an electronic/engine control module (ECM), a powergain control module (PCM), a transmission control module (TCM), a brake control module (BCM or EBCM), a central control module (CCM), a central timing module (CTM), a general electronic module (GEM), a body control module (BCM), a suspension control module (SCM), or the like.

In some implementations, ECU 220 may be connected to magnetic sensor 215 such that ECU 220 may receive profile information, safe-state information, and/or diagnosis information, associated with magnetic sensor 215, via one or more transmission interfaces and/or via one or more output terminals. In some implementations, ECU 220 may be capable of calibrating, controlling, adjusting, or the like, the one or more electrical systems and/or electrical subsystems based on the information transmitted by magnetic sensor 215.

As shown in FIG. 2B, example environment 200 may alternatively include magnetic sensor 215, ECU 220, and encoder wheel 225 (e.g., rather than tooth wheel 205 and magnet 210). Encoder wheel 225 may include a magnetic pole wheel with at least two alternating poles, such as a north pole and a south pole. In some implementations, encoder wheel 225 may produce a magnetic field. In some implementations, encoder wheel 225 may be attached to or coupled with an object for which a speed and/or a position is to be measured, such as a cylindrical structure (e.g., a crankshaft, a camshaft, a rotating cylinder, etc.), a wheel structure (e.g., associated with a tire), an axle (e.g., a vehicle axle), or the like.

In some implementations, the alternating poles of encoder wheel 225 may be on a first section of a circumference of encoder wheel 225 (e.g., comparable to the first section of tooth wheel 205 that includes the set of teeth), while a second section of the circumference of encoder wheel 225 may include only one of the alternating poles that represent a reference zone gap of encoder wheel 225 (e.g., comparable to the second section of tooth wheel 205 that does not include any teeth).

The number and arrangement of apparatuses shown in FIGS. 2A and 2B are provided as an example. In practice, there may be additional apparatuses, fewer apparatuses, different apparatuses, or differently arranged apparatuses than those shown in FIGS. 2A and 2B. Furthermore, two or more apparatuses shown in FIGS. 2A and 2B may be implemented within a single apparatus, or a single apparatus shown in FIGS. 2A and 2B may be implemented as multiple, distributed apparatuses. Additionally, or alternatively, a set of apparatuses (e.g., one or more apparatuses) of environment 200 may perform one or more functions described as being performed by another set of apparatuses of environment 200.

FIG. 3 is a diagram of example components of a magnetic sensor 215 included in example environment 200 of FIGS. 2A and 2B. As shown, magnetic sensor 215 may include a sensing element 310, an analog-to-digital convertor (ADC) 320, a digital signal processor (DSP) 330, a memory component 340, and a digital interface 350.

Sensing element 310 may include one or more components for sensing an intensity of a magnetic field applied to magnetic sensor 215. For example, sensing element 310 may include a Hall sensor that operates based on a Hall-effect. As another example, sensing element 310 may include a magnetoresistance (MR) sensor, comprised of a magnetoresistive material (e.g., nickel iron (NiFe)), where the electrical resistance of the magnetoresistive material may depend on a strength and/or a direction of the magnetic field applied to the magnetoresistive material. Here, sensing element 310 may measure magnetoresistance based on an anisotropic magnetoresistance (AMR) effect, a giant magnetoresistance (GMR) effect, a tunnel magnetoresistance (TMR) effect, or the like. As an additional example, sensing element 310 may include a variable reluctance (VR) sensor that operates based on induction. In some implementations, sensing element 310 may provide an analog signal, corresponding to the external magnetic field, to ADC 320.

ADC 320 may include an analog-to-digital converter that converts an analog signal from sensing element 310 to a digital signal. For example, ADC 320 may convert analog signals, received from sensing element 310, into digital signals to be processed by DSP 330. ADC 320 may provide the digital signals to DSP 330. In some implementations, magnetic sensor 215 may include one or more ADCs 320.

DSP 330 may include a digital signal processing device or a collection of digital signal processing devices. In some implementations, DSP 330 may receive a digital signal from ADC 320 and may process the digital signal to form an output (e.g., destined for ECU 220), such as an output in the form of a signal that includes a set of voltage pulses and/or a set of current pulses.

Memory 340 may include a read only memory (ROM) (e.g., an EEPROM), a random access memory (RAM), and/or another type of dynamic or static storage device (e.g., a flash memory, a magnetic memory, an optical memory, etc.) that stores information and/or instructions for use by magnetic sensor 215. In some implementations, memory 340 may store information associated with processing performed by DSP 330.

Digital interface 350 may include an interface via which magnetic sensor 215 may receive and/or provide information from and/or to another device, such as ECU 220. For example, digital interface may provide the output determined by DSP 330 to ECU 220 in the form of an output voltage, an output current, or the like. In some implementations, magnetic sensor 215 may include a set of digital interfaces, where one or more digital interfaces, in the set of digital interfaces, may be associated with one or more output terminals of magnetic sensor 215.

The number and arrangement of components shown in FIG. 3 are provided as an example. In practice, magnetic sensor 215 may include additional components, fewer components, different components, or differently arranged components than those shown in FIG. 3. Additionally, or alternatively, a set of components (e.g., one or more components) of magnetic sensor 215 may perform one or more functions described as being performed by another set of components of magnetic sensor 215.

FIG. 4 is a flow chart of an example process for transmitting, during a rotation of a magnet wheel, a set of output pulses that corresponds to safe-state information and/or diagnosis information associated with the magnet wheel. While example process 400 is described in the context of a magnet wheel in the form of tooth wheel 205, example process 400 may also apply in the context of a magnet wheel in the form of encoder wheel 225.

As shown in FIG. 4, process 400 may include sensing a magnetic field during a rotation of a magnet wheel (block 410). For example, magnetic sensor 215 may sense a magnetic field during a rotation of tooth wheel 205.

In some implementations, the magnetic field, sensed by magnetic sensor 215, may vary based on the rotation of tooth wheel 205. For example, assume that magnetic sensor 215 is positioned to sense a magnetic field produced by magnet 210, and the magnet 210 is positioned such that the magnetic field, produced by magnet 210, is distorted by each tooth of tooth wheel 205 (e.g., an intensity of the magnetic field increases or decreases as a tooth passes magnet 210). Here, magnetic sensor 215 may sense the magnetic field, produced by magnet 210, that includes distortions corresponding to the teeth of tooth wheel 205.

In some implementations, magnetic sensor 215 may transmit profile information based on the sensed magnetic field, as described below. The profile information may include information that corresponds to a rotational position of tooth wheel 205 during the rotation. Additionally, or alternatively, magnetic sensor 215 may determine and transmit safe-state information and/or diagnosis information, associated with the magnetic sensor 215, based on the sensed magnetic field, as described below.

In some implementations, such as in a crankshaft context, magnetic sensor 215 may identify a reference zone gap of tooth wheel 205 based on the sensed magnetic field. For example, magnetic sensor 215 may sense the magnetic field during multiple rotations of tooth wheel 205, and may determine, based on the sensed magnetic field, a period of time, associated with each rotation, that corresponds to the reference zone gap (e.g., by identifying periods of time during which no tooth is detected). Similarly, magnetic sensor 215 may identify a number of teeth on tooth wheel 205 (e.g., such that magnetic sensor 215 may count the teeth in order to identify a full rotation at a later time). Additionally, or alternatively, magnetic sensor 215 may identify one or more tooth gaps associated with tooth wheel 205 based on the sensed magnetic field.

In some implementations, such as in a camshaft context, magnetic sensor 215 may identify a longest tooth gap of tooth wheel 205 based on the sensed magnetic field. For example, magnetic sensor 215 may sense the magnetic field during multiple rotations of tooth wheel 205, and may determine, based on the sensed magnetic field, a period of time, associated with each rotation, that corresponds to a longest tooth gap between two teeth of tooth wheel 205 (e.g., by identifying periods of time during which no tooth is detected).

As shown in FIG. 4, process 400 may include determining, based on the sensed magnetic field, safe-state information and/or diagnosis information associated with a magnetic sensor and/or the magnet wheel (block 420). For example, magnetic sensor 215 may determine, based on the sensed magnetic field, safe-state information and/or diagnosis information associated with magnetic sensor 215 and/or tooth wheel 205 (herein referred to as safe-state/diagnosis information). In some implementations, magnetic sensor 215 may determine the safe-state/diagnosis information during the rotation of tooth wheel 205 (e.g., in real-time, in near real-time, etc.). Additionally, or alternatively, magnetic sensor 215 may determine the safe-state/diagnosis information at a later time (e.g., after the rotation of tooth wheel 205, based on a request from ECU 220, etc.).

The safe-state information may include information indicating that magnetic sensor 215 has detected a potential problem associated with magnetic sensor 215 and/or tooth wheel 205. For example, the safe-state information may include information indicating that a speed signal, determined based on the sensed magnetic field for use in identifying a rotational speed of tooth wheel 205, is approaching or has reached a speed signal threshold (e.g., where magnetic sensor 215 may be unable to ensure accurate determination of the rotational speed of tooth wheel 205 when the speed signal satisfies the speed signal threshold).

As another example, the safe-state information may include information indicating that a direction signal, determined based on the sensed magnetic field for use in identifying a direction of the rotation of tooth wheel 205, is approaching or has reached a direction signal threshold (e.g., where magnetic sensor 215 may be unable to ensure accurate determination of the direction of tooth wheel 205 when the direction signal satisfies the direction signal threshold). As still another example, the safe-state information may indicate that the direction signal satisfies the direction signal threshold (e.g., that magnetic sensor 215 is unable to determine the direction of the rotation), and/or that the speed signal does not satisfy the speed signal threshold (e.g., that magnetic sensor 215 may accurately determine the speed of the rotation).

As yet another example, the safe-state information may indicate that an air gap between tooth wheel 205 and magnetic sensor 215 is at or near an air gap threshold (e.g., where magnetic sensor 215 may be unable to ensure accurate sensing of the magnetic field when the air gap threshold is satisfied). These are just some examples of types of safe-state information. Other types of safe-state information are possible.

The diagnosis information may include information that identifies a cause for a potential problem detected magnetic sensor 215. For example, the diagnosis information may include information that identifies a lowest amplitude of the magnetic field during a rotation of tooth wheel 205 (e.g., a worst amplitude, corresponding to a particular tooth, that may cause the speed signal to approach or reach the speed signal threshold). As another example, the diagnosis information may include information that identifies a lowest amplitude of the direction signal during a rotation of tooth wheel 205 (e.g., a worst signal amplitude that may be causing the direction signal to approach or reach the direction signal threshold).

As an additional example, the diagnosis information may include a type of information that may not be directly related to the measurement of tooth wheel 205, such as temperature information associated with magnetic sensor 215 (e.g., due to the linearity of GMR, GMR may be used to obtain temperature information associated with magnetic sensor 215). In such a case, magnetic sensor 215 may include a temperature compensation function, which may enable magnetic sensor 215 to transmit, as diagnosis information, information indicating that a temperature threshold has been satisfied.

As yet another example, the diagnosis information may include sensor status/failure information, such as information indicating whether a supply voltage of magnetic sensor 215 has satisfied a threshold (e.g., when the supply voltage is too high, when the supply voltage is too low, etc.), information indicating that data, stored by magnetic sensor 215, is corrupted (e.g. via error-correcting code (ECC), cyclic redundancy check (CRC), parity check etc), or the like. These are just some examples of types of diagnosis information. Other types of diagnosis information are possible.

In some implementations, the diagnosis information may include a data record that magnetic sensor 215 may transmit during multiple rotations of tooth wheel 205. For example, assume that magnetic sensor 215 is configured to transmit three bits of information during a period of time corresponding to a reference zone of tooth wheel 205. Further, assume that magnetic sensor 215 is configured to transmit a data record that comprises a 16 bit data word. In this example, the data record may include the 16 bit data word, and magnetic sensor 215 may transmit the data record during multiple (e.g., consecutive) rotations of tooth wheel 205, in the manner described below, such as by transmitting one bit for each of 16 rotations of tooth wheel 205, two bits for each of eight rotations of tooth wheel 205, or the like.

In some implementations, magnetic sensor 215 may determine the safe-state/diagnosis information based on the sensed magnetic field. For example, magnetic sensor 215 may sense the magnetic field for one or more rotations of tooth wheel 205, and may determine, based on analyzing values corresponding to the sensed magnetic field, the speed signal, the direction signal, or the like, and may determine the safe-state/diagnosis information, accordingly.

As shown in FIG. 4, process 400 may include outputting a first set of output pulses that corresponds to profile information for the magnet wheel (block 430). For example, magnetic sensor 215 may output a first set of output pulses that corresponds to profile information for tooth wheel 205. In some implementations, magnetic sensor 215 may output the first set of output pulses during the rotation of tooth wheel 205 (e.g., in real-time, in near real-time, etc.). Additionally, or alternatively, magnetic sensor 215 may output the first set of output pulses at another time.

In some implementations, the first set of output pulses may include a set of voltage pulses. For example, magnetic sensor 215 may be configured to transmit the profile information to ECU 220 by outputting, via a voltage interface of an output terminal connected to ECU 220, a set of voltage pulses, where each voltage pulse may correspond to a tooth of tooth wheel 205. Here, upon sensing a leading edge of a tooth, magnetic sensor 215 may output a voltage pulse, of the set of voltage pulses, by causing a voltage of a signal, transmitted via the voltage interface, to change from a first level (e.g., a high level, such as 5 volts (V)) to a second level (e.g., a low level, such as 0 V) for a period of time. In some implementations, as described above, the period of time of the voltage pulse (i.e., the pulse length) may depend on a direction of the rotation of tooth wheel 205. For example, magnetic sensor 215 may output a 45 μs voltage pulse when tooth wheel 205 is rotating in a forward direction, and may provide a 90 μs voltage pulse when tooth wheel is rotating in a rearward direction. Here, the voltage pulse may be a particular length that does not represent the width of the tooth (i.e., magnetic sensor 215 transmits the pulse, of the particular length, when magnetic sensor 215 senses the leading edge of the tooth). However, in some implementations, the voltage pulse may represent the width of the tooth (i.e., magnetic sensor 215 transmits a pulse corresponding to the width of the tooth length based on sensing the leading edge of the tooth and the trailing edge of the tooth).

Alternatively, the first set of output pulses may include a set of current pulses. For example, magnetic sensor 215 may be configured to transmit the profile information to ECU 220 by outputting, via a current interface of the output terminal connected to ECU 220, a set of current pulses, where each current pulse may correspond to a tooth of tooth wheel 205. Here, magnetic sensor 215 may output a current pulse, of the set of current pulses, by causing a current of a signal, transmitted via the current interface, to change from a first level (e.g., a high level, such as 14 milliamps (mA)) to a second level (e.g., a low level, such as 7 mA) for a period of time. In some implementations, as described above, the pulse length may depend on a direction of the rotation of tooth wheel 205.

As shown in FIG. 4, process 400 may include outputting a second set of output pulses that represents the safe-state information and/or the diagnosis information (block 440). For example, magnetic sensor 215 may output a second set of output pulses that represents the safe-state/diagnosis information. In some implementations, magnetic sensor 215 may output the second set of output pulses during the rotation of tooth wheel 205, such as during a time period corresponding to the reference zone gap, one or more time periods corresponding to one or more tooth gaps of tooth wheel 205, concurrently with outputting the first set of output pulses, based on a request from ECU 220, or the like, as described below.

The second set of output pulses may include one or more pulses (e.g., voltage pulses, current pulses, etc.) that represent the safe-state/diagnosis information. For example, magnetic sensor 215 may store or have access to information associated with encoding the safe-state/diagnosis information in the form of one or more voltage pulses. Here, magnetic sensor 215 may output, via a voltage interface, the set of voltage pulses that represent the safe-state/diagnosis information. ECU 220 may receive the voltage pulses, and may interpret (e.g., based on the information associated with encoding the safe-state/diagnosis information) the one or more voltage pulses in order to determine the safe-state/diagnosis information. Additional details regarding the second set of output pulses are described in the below examples.

In some implementations, magnetic sensor 215 may output the second set of output pulses during a time period corresponding to the reference zone gap. For example, assume that magnetic sensor 215 is a three-wire sensor that includes a supply terminal, a ground terminal, and an output terminal. Further, assume that magnetic sensor 215 is configured to output a first set of voltage pulses, via a voltage interface associated with the output terminal, that corresponds to profile information associated with tooth wheel 205. In this example, magnetic sensor 215 may output a second set of voltage pulses during a time period corresponding to a reference zone gap of tooth wheel 205 and via the voltage interface associated with the output terminal. In some implementations, a cost (e.g., a monetary cost, in processing resources, in memory resources, in time to configuration magnetic sensor 215 and/or ECU 220, etc.), associated with magnetic sensor 215, may be reduced when magnetic sensor 215 is configured to transmit the second set of output pulses during the time period corresponding to the reference zone gap (e.g., since no additional interfaces and/or terminals may be needed).

In some implementations, the second set of output pulses may include a single output pulse that represents a sequence of bits of the safe-state/diagnosis information. For example, magnetic sensor 215 may be configured to output one of eight different pulse lengths (e.g., 45 µs, 75 µs, 105 µs, 135 µs, 165 µs, 195 µs, 225 µs, or 255 µs) during the reference zone gap time period, where each of the multiple different pulse lengths may represent a sequence of three bits (e.g., 000, 001, 010, 100, 011, 101, 110, or 111) of the safe-state/diagnosis information. As another example, magnetic sensor 215 may be configured to output one of 16 different pulse lengths, one of 32 different pulse lengths, one of 64 different pulse lengths, or the like, where each of the 16, 32, or 64 different pulse lengths represents a sequence of four bits, five bits, or six bits, respectively.

In some implementations, a maximum frequency of the rotation of tooth wheel 205 may govern the number of possible different pulse lengths that may be output by magnetic sensor 215 during the time period associated with the reference zone gap. For example, for tooth wheel 205 with 58 teeth and a two-tooth reference zone gap that may rotate at up to 10,000 rotations per minute (rpm) (i.e., 10 kilohertz (kHz)), the reference zone gap may be limited to a maximum of 300 µs. As such, magnetic sensor 215 may be configured to output one of eight multiple different output pulses that represents a sequence of three bits, as described in the above example. As other examples, for tooth wheel 205 that may rotate at up to 5 kHz, 2.5 kHz, 1.25 kHz, or 625 Hz, the reference zone gap may be limited to 600 µs, 1200 µs, 2400 µs, or 4800 µs, respectively. In these examples, magnetic sensor 215 may be configured to output one of 16, 32, 64, or 128 different output pulses that represents a sequence of four bits, five bits, six bits, or seven bits, respectively.

In some implementations, an output pulse may represent one or more different bits of the safe-state/diagnosis information. For example, when the pulse length is one of eight possible pulse lengths that represent three bits of information, the first bit of information may include a first bit of safe-state information, the second bit may include a second bit of safe-state information, and the third bit may include a bit of diagnosis information (e.g., a single bit, a bit included in a data record, etc.). The manner in which magnetic sensor 215 transmits the safe-state/diagnosis information may be configurable.

Additionally, or alternatively, magnetic sensor 215 may output the second set of output pulses during one or more time periods corresponding to one or more tooth gaps of tooth wheel 205. For example, assume that magnetic sensor 215 is a three-wire sensor that includes a supply terminal, a ground terminal, and an output terminal. Further, assume that magnetic sensor 215 is configured to output a first set of voltage pulses, via a voltage interface associated with the output terminal, that corresponds to profile information associated with tooth wheel 205, as described above. In this example, magnetic sensor 215 may output a second set of voltage pulses during time periods corresponding to the one or more tooth gaps of tooth wheel 205 (e.g., multiple tooth gaps of a symmetrical tooth wheel 205, a longest tooth gap of an asymmetrical tooth wheel 205, etc.) and via the same voltage interface associated with the output terminal. In some implementations, a cost (e.g., a monetary cost, in processing resources, in memory resources, in time to configuration magnetic sensor 215 and/or ECU 220, etc.), associated with magnetic sensor 215, may be reduced when magnetic sensor 215 is configured to transmit the second set of output pulses during the time periods corresponding to the tooth gaps (e.g., since no additional interfaces and/or terminals may be needed).

As a particular example, assume that magnetic sensor 215 is configured to output the first set of output pulses by causing a voltage of the signal, transmitted via the voltage interface, to change from a first level (e.g., 5V) to a second level (e.g., 0V) for a period of time (e.g., 45 µs) based upon detecting an end of each tooth. Here, magnetic sensor 215, when outputting the second set of output pulses, may cause magnetic sensor 215 to change the voltage of the signal from the first level to a third level (e.g., 2V) (e.g., rather than from the first level to the second level), during the period of time, to represent a bit of the safe-state/diagnosis information. In this example, ECU 220 may be configured to interpret the voltage signal being at the third level as a first value (e.g., 1) and the voltage signal being at the second level to be a second value (e.g., 0).

In another example implementation, magnetic sensor 215 may be configured to output the first set of output pulses at a first level (e.g., 4V) or a second level (e.g., 0V), and the second set of output pulses at a third level (e.g., 3V) or a fourth level (e.g., 1.5V). Here, ECU 220 may be configured to interpret the voltage of the signal being at the first level or the second level as indicating that magnetic sensor 215 is not providing any safe-state/diagnosis information, but may be configured to interpret the voltage of the signal being at the third level as a first bit value of the safe-state/diagnosis information (e.g., 1) and the voltage signal being at the fourth level as a second bit value of the safe-state/diagnosis information (e.g., 0). Additionally, or alternatively, magnetic sensor 215 may be configured to output the second set of output voltages during the periods of time associated with the tooth gaps using another modulation scheme.

Additionally, or alternatively, magnetic sensor 215 may output the second set of output pulses via a different transmission interface than the first set of output pulses. For example, assume that magnetic sensor 215 is a three-wire sensor that includes a supply terminal, a ground terminal, and an output terminal. Further, assume that magnetic sensor 215 is configured to output a set of voltage pulses, via a voltage interface of the output terminal, that corresponds to profile information associated with tooth wheel 205, as described above. In this example, magnetic sensor 215 may output a set of current pulses, via a current interface of the output terminal, that represents the safe-state/diagnosis information. For example, magnetic sensor 215 may output, via the current interface, a set of current pulses that represent one or more start bits (e.g., an initial word), one or more error detection bits (e.g., a cyclic redundancy check (CRC) word), a sequence of bits of the safe-state/diagnosis information (e.g., a data word), and one or more stop bits (e.g., a stop word). Magnetic sensor 215 may then output additional sets of current pulses to transmit additional bits of the safe-state/diagnosis information. Here, magnetic sensor 215 may output the set of current pulses at any time during and/or after the rotation (e.g., synchronously, asynchronously, based on a request from ECU 220, etc.) since the set of output pulses is independent of the set of current pulses. In this way, magnetic sensor 215 may output the set of voltage pulses and the set of current pulses via different interfaces of a single output terminal. In some implementations, the availability of times during which to transmit the safe-state/diagnosis information may increase when magnetic sensor 215 is configured to transmit the second set of output pulses via the different transmission interface (e.g., since transmission of the second set of output pulses need not be timed based on the first set of output pulses).

Additionally, or alternatively, magnetic sensor 215 may output the second set of output pulses via a different output terminal than the first set of output pulses. For example, assume that magnetic sensor 215 is a four-wire sensor that includes a supply terminal, a ground terminal, a first output terminal, and a second output terminal. Further, assume that magnetic sensor 215 is configured to output a first set of voltage pulses, via the first output terminal, that corresponds to profile information associated with tooth wheel 205, as described above. In this example, magnetic sensor 215 may output a second set of voltage pulses, via the second output terminal, that represents the safe-state/diagnosis information. For example, magnetic sensor 215 may output, via the second output terminal, a set of voltage pulses that represents one or more start bits (e.g., an initial word), one or more error detection bits (e.g., a CRC word), a sequence of bits of the safe-state/diagnosis information (e.g., a data word), and one or more stop bits (e.g., a stop word). In some implementations, the availability of times during which to transmit the safe-state/diagnosis information may increase when magnetic sensor 215 is configured to transmit the second set of output pulses via the different output terminal (e.g., since transmission of the second set of output pulses need not be timed based on the first set of output pulses).

Magnetic sensor 215 may then output additional sets of output pulses that represent additional bits of the safe-state/diagnosis information. Here, magnetic sensor 215 may output the second set of voltage pulses at any time during and/or after the rotation (e.g., synchronously, asynchronously, based on a request from ECU 220, etc.) since the second set of voltage pulses is provided independently of the first set of voltages pulses. In this way, magnetic sensor 215 may output the first set of output pulses and the second set of output pulses via a first output terminal and a second output terminal, respectively. In another example implementation, magnetic sensor 215 may output the first set of output pulses and the second set of output pulses in the form of a first set of current pulses via the first output terminal and a second set of current pulses via the second output terminal. In another example implementation, magnetic sensor 215 may output the first set of output pulses and the second set of output pulses in the form of a set of voltage pulses via the first output terminal and a set of current pulses via the second output terminal.

In some implementations, one or more of the above example implementations may be combined to allow magnetic sensor 215 to provide the safe-state/diagnosis information. For example, magnetic sensor 215 may output, via a first output terminal during a time period associated with a reference zone gap, a set of voltage pulses that represents a first portion of the safe-state/diagnosis information, while concurrently outputting, via a second output terminal, a set current pulses that represents a second portion of the safe-state/diagnosis information.

In some implementations, ECU 220 may receive the second set of output pulses, and may interpret (e.g., based on information stored or accessible by ECU 220) the second set of output pulses to determine the safe-state/diagnosis information, accordingly. In this way, magnetic sensor 215 may transmit safe-state information and/or diagnosis information without compromising an ability of magnetic sensor 215 to transmit profile information associated with tooth wheel 205.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5A:
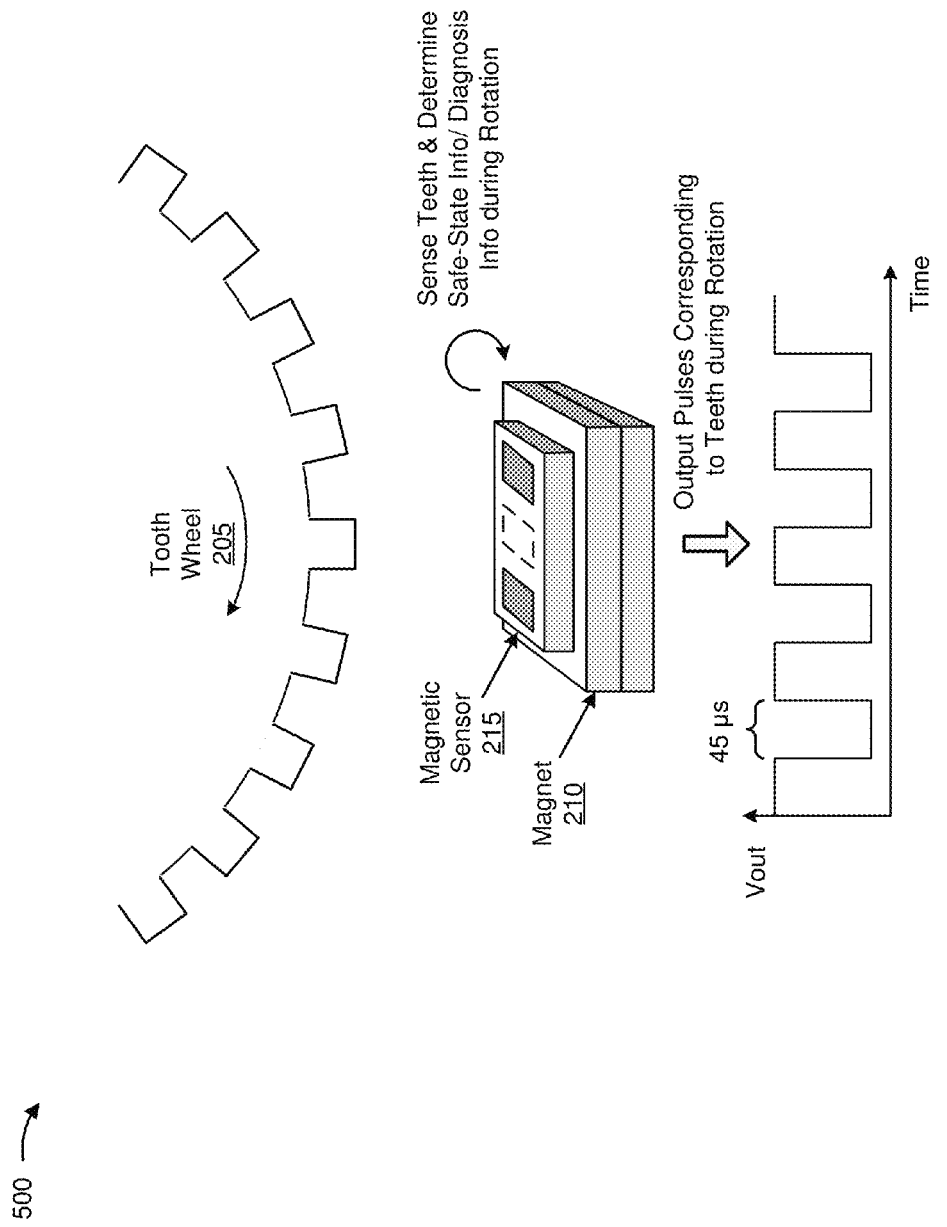
FIGS. 5A and 5B are diagrams of an example implementation of a magnetic sensor that transmits safe-state information and/or diagnosis information, associated with the magnetic sensor and/or a magnet wheel, via a set of voltage pulses during a time period corresponding to a reference zone gap of the magnet wheel.
Figure 5B:
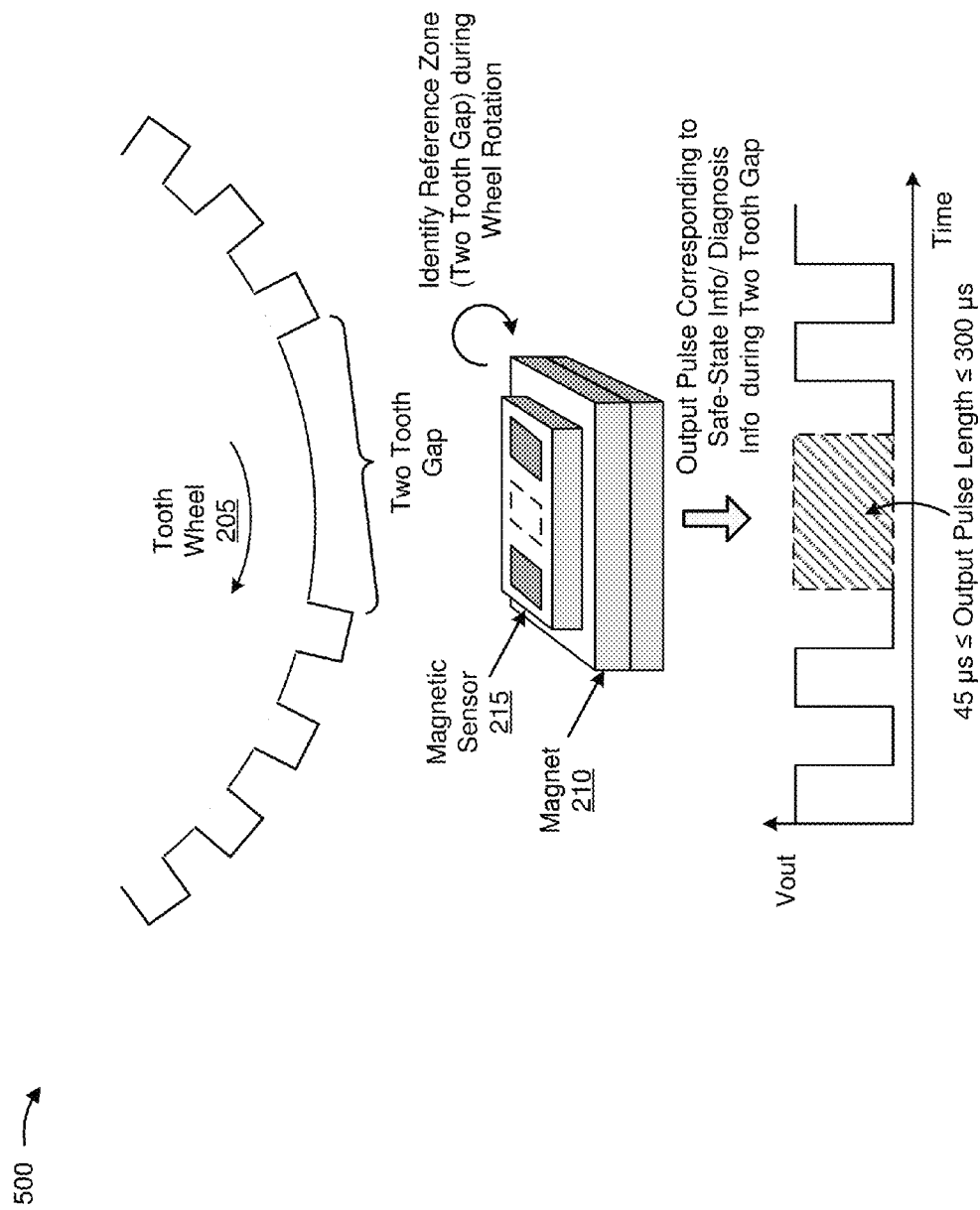

FIGS. 5A and 5B are diagrams of an example implementation 500 of magnetic sensor 215 that transmits safe-state information and/or diagnosis information, associated with tooth wheel 205, via a set of voltage pulses during a time period corresponding to a reference zone of tooth wheel 205. For the purposes of example implementation 500, assume that magnetic sensor 215 is positioned to sense a magnetic field, generated by magnet 210 and distorted by tooth wheel 205, and that tooth wheel 205 includes a set of teeth on a first section of a circumference of tooth wheel 205 and a reference zone gap on a second section of the circumference of tooth wheel 205. Further, assume that magnetic sensor 215 is configured to output, to ECU 220 and during a rotation of the wheel, a signal that represents profile information of tooth wheel 205 (e.g., a signal that identifies each tooth as detected by magnetic sensor 215).

As shown in FIG. 5A, tooth wheel 205 may rotate in a particular (e.g., clockwise) direction, and magnetic sensor 215 may sense the magnetic field produced by magnet 210 and distorted by tooth wheel 205. As shown, magnetic sensor 215 may determine, based on the magnetic field sensed during the rotation of tooth wheel 205, safe-state information and/or diagnosis information associated with magnetic sensor 215 and/or tooth wheel 205.

As further shown in FIG. 5A, magnetic sensor 215 may transmit, during the rotation of tooth wheel 205, a signal that represents the profile of tooth wheel 205. For example, as shown, magnetic sensor 215 may modify a signal by outputting a 45 µs voltage pulse associated with each tooth of tooth wheel 205 (e.g., where each falling edge of the signal may identify an end of a tooth).

As shown in FIG. 5B, magnetic sensor 215 may identify the reference zone gap associated with the second section of the circumference of tooth wheel 205. As further shown, within a time period corresponding to the reference zone gap of tooth wheel 205, magnetic sensor 215 may modify the signal to transmit the safe-state/diagnosis information by outputting a voltage pulse (e.g., with pulse length between 45 µs and 300 µs (inclusive)) during the time period associated with the reference zone gap. In this example, ECU 220 may be configured to receive the voltage pulse associated with the reference zone gap, and may determine the safe-state/diagnosis information based on a pulse length of the reference zone gap pulse (e.g., by interpreting the pulse length as a sequence of bits based on information stored by ECU 220).

As indicated above, FIGS. 5A and 5B are provided merely as an example. Other examples are possible and may differ from what was described with regard to FIGS. 5A and 5B.

Figure 6:
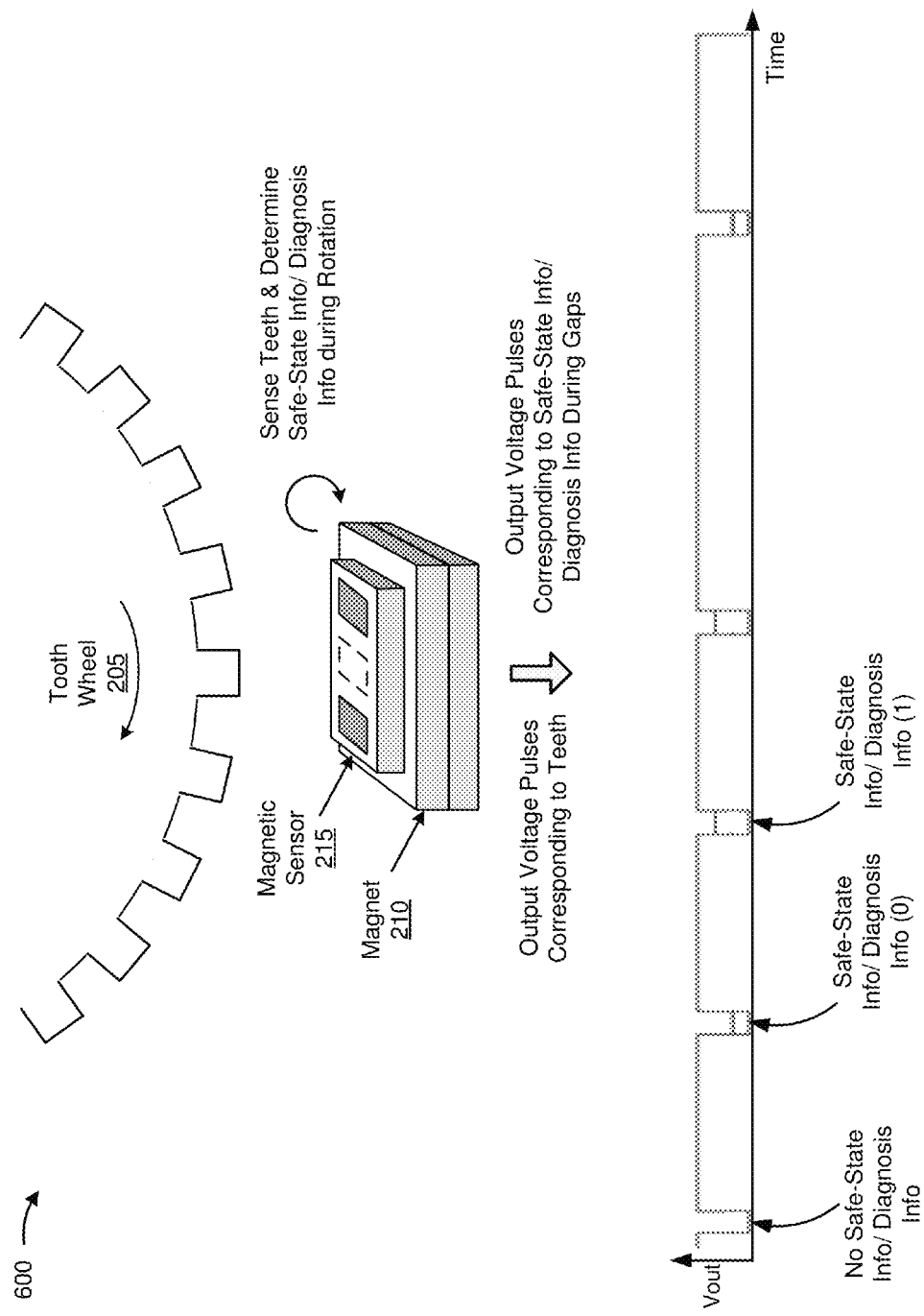
FIG. 6 is a diagram of an example implementation of a magnetic sensor that transmits safe-state information and/or diagnosis information, associated with the magnetic sensor and/or a magnet wheel, via a set of voltage pulses within time periods corresponding to one or more tooth gaps associated with the magnet wheel.

FIG. 6 is a diagram of an example implementation 600 of magnetic sensor 215 that transmits safe-state information and/or diagnosis information, associated with tooth wheel 205, via a set of voltage pulses within time periods corresponding to one or more tooth gaps associated with tooth wheel 205. For the purposes of example implementation 600, assume that magnetic sensor 215 is positioned to sense a magnetic field, generated by magnet 210 and distorted by tooth wheel 205, and that tooth wheel 205 includes a set of teeth on a circumference of tooth wheel 205. Further, assume that magnetic sensor 215 is configured to output, to ECU 220 and during a rotation of the wheel, a signal that represents profile information of tooth wheel 205 (e.g., a signal that identifies each tooth as detected by magnetic sensor 215).

As shown in FIG. 6, tooth wheel 205 may rotate in a particular (e.g., clockwise) direction, and magnetic sensor 215 may sense the magnetic field produced by magnet 210 and distorted by tooth wheel 205. As shown, magnetic sensor 215 may determine, based on the magnetic field sensed during the rotation of tooth wheel 205, profile information associated with tooth wheel 205 and safe-state information and/or diagnosis information associated with magnetic sensor 215 and/or tooth wheel 205.

As further shown in FIG. 6, magnetic sensor 215 may transmit, during the rotation of tooth wheel 205, a signal that represents the profile of tooth wheel 205. For example, as shown, magnetic sensor 215 may modify a signal by outputting a 45 µs voltage pulse associated with each tooth of tooth wheel 205 (e.g., where each falling edge of the signal may identify an end of a tooth). For example, magnetic sensor 215 may output each voltage pulse, of the first set of voltage pulses, by causing a voltage level of the signal to change from a first level (e.g., 5V) to a second level (e.g., 0 V).

As further shown in FIG. 6, magnetic sensor 215 may identify each tooth gap of the circumference of tooth wheel 205. As shown, within one or more time periods corresponding to tooth gaps of tooth wheel 205 (e.g., time periods during which the first set of voltage pulses may be provided), magnetic sensor 215 may modify the signal to transmit the safe-state/diagnosis information by outputting a voltage pulse in accordance with a voltage modulation scheme stored or accessible by magnetic sensor 215. For example, magnetic sensor 215 may output each voltage pulse, of the second set of voltage pulses, by causing the voltage level of the signal to change from the first level (e.g., 5V) to a third level (e.g., 1.5V) to represent a first bit of the safe-state/diagnosis information (e.g., 0), and/or by causing the voltage level of the signal to change from the first level to a fourth level (e.g., 3V) to represent a second bit of the safe-state/diagnosis information (e.g., 1). Here, the second set of voltage pulses may override the first set of voltage pulses (e.g., such that magnetic sensor 215 outputs the signal at the second level only when magnetic sensor 215 is not transmitting any safe-state/diagnosis information).

In this example, ECU 220 may be configured to receive the voltage pulses associated with the tooth gaps, and may determine the safe-state/diagnosis information accordingly. For example, when the voltage pulse is at the second level (e.g., 0V), ECU may determine that magnetic sensor 215 is not transmitting any safe-state/diagnosis information. As another example, when the voltage pulse is at the third level (e.g., 1.5V), ECU 220 may determine that magnetic sensor 215 is transmitting safe-state/diagnosis information with the first bit value (e.g., 0). As a final example, when the voltage pulse is at the fourth level (e.g., 3V), ECU 220 may determine that magnetic sensor 215 is transmitting safe-state/diagnosis information with the second bit value (e.g., 1).

As indicated above, FIG. 6 is provided merely as an example. Other examples are possible and may differ from what was described with regard to FIG. 6.

Figure 7:
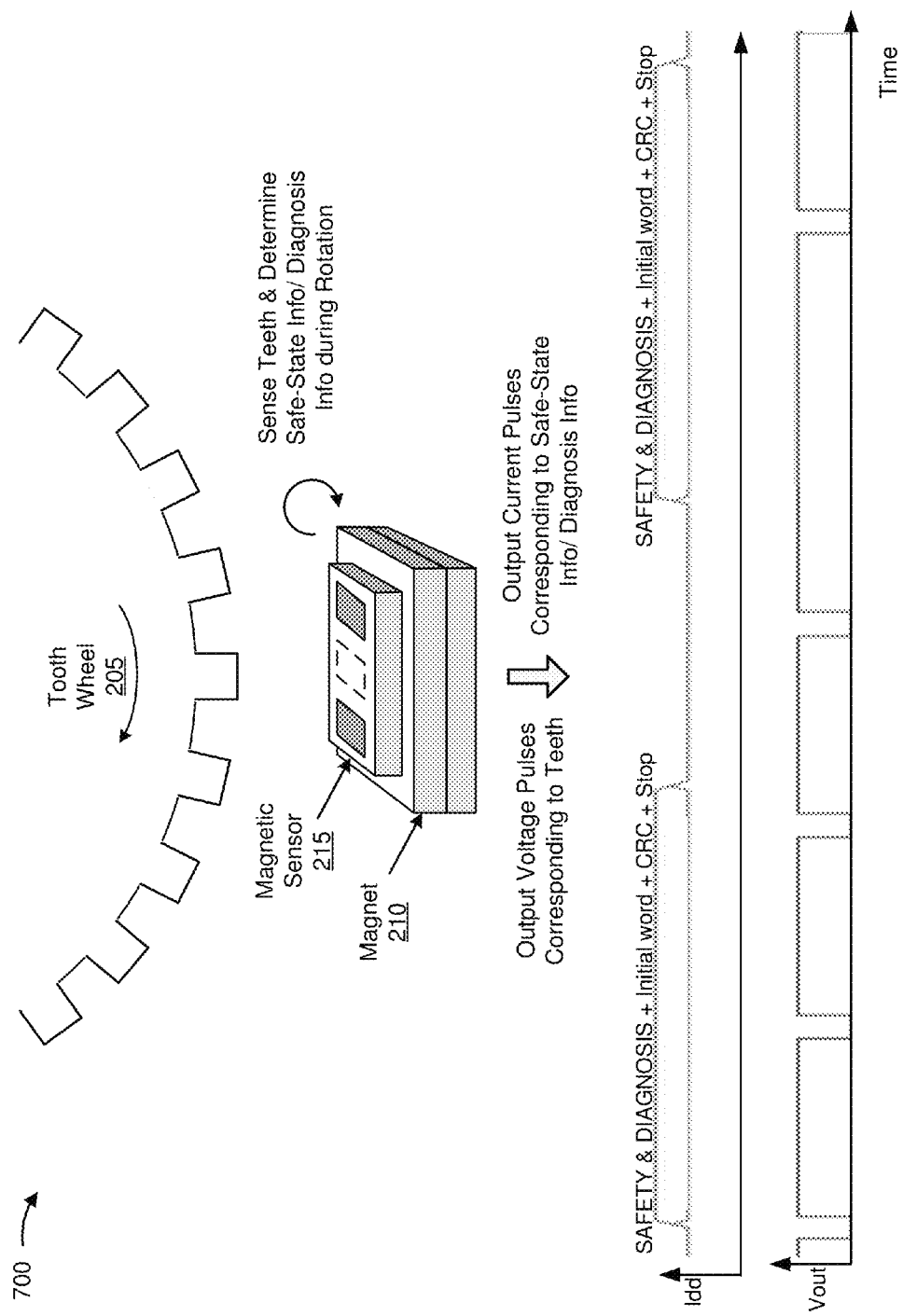
FIG. 7 is a diagram of an example implementation of a magnetic sensor that transmits profile information, associated with a magnet wheel, and safe-state information and/or diagnosis information, associated with the magnetic sensor and/or the magnet wheel, via a first transmission interface associated with an output terminal and second transmission interface associated with the output terminal, respectively.

FIG. 7 is a diagram of an example implementation 700 of magnetic sensor 215 that transmits profile information, associated with tooth wheel 205, and safe-state/diagnosis information, associated with magnetic sensor 215 and/or tooth wheel 205, via a first transmission interface of an output terminal and a second transmission interface of the output terminal, respectively. For the purposes of example implementation 700, assume that magnetic sensor 215 is positioned to sense a magnetic field, generated by magnet 210 and distorted by tooth wheel 205, and that tooth wheel 205 includes a set of teeth on a circumference of tooth wheel 205. Further, assume that magnetic sensor 215 is configured to output, to ECU 220 and during a rotation of the wheel, a signal that represents profile information of tooth wheel 205 (e.g., a signal that identifies each tooth as detected by magnetic sensor 215).

As shown in FIG. 7, tooth wheel 205 may rotate in a particular (e.g., clockwise) direction, and magnetic sensor 215 may sense the magnetic field produced by magnet 210 and distorted by tooth wheel 205. As shown, magnetic sensor 215 may determine, based on the magnetic field sensed during the rotation of tooth wheel 205, safe-state information and/or diagnosis information associated with magnetic sensor 215 and/or tooth wheel 205.

As further shown in FIG. 7, magnetic sensor 215 may transmit, during the rotation of tooth wheel 205, a signal that represents the profile of tooth wheel 205. For example, as shown, magnetic sensor 215 may modify a signal, transmitted via an output terminal of magnetic sensor 215, by outputting a 45 μs voltage pulse associated with each tooth of tooth wheel 205 (e.g., where each falling edge of the signal may identify an end of a tooth).

As further shown in FIG. 7, magnetic sensor 215 may also transmit a second set of output pulses that represents the safe-state/diagnosis information. For example, as shown by FIG. 7, magnetic sensor 215 may output a set of current pulses, via the output terminal, that represents the safe-state/diagnosis information. Here, magnetic sensor 215 may output, via the output terminal, a set of current pulses that represent an initial word, a CRC word, a sequence of bits of the safe-state/diagnosis information, and a stop word. Magnetic sensor 215 may then output additional sets of current pulses that represent additional bits of the safe-state/diagnosis information. As shown, magnetic sensor 215 may output the set of current pulses at any time during and/or after the rotation of tooth wheel 205 since the set of current pulses is provided via a different transmission interface associated with the output terminal (i.e., independent of the set of voltage pulses). In this example, ECU 220 may be configured to receive the set of current pulses, and may determine the safe-state/diagnosis information based on interpreting the set of current pulses in accordance with a current modulation scheme stored or accessible by ECU 220.

As indicated above, FIG. 7 is provided merely as an example. Other examples are possible and may differ from what was described with regard to FIG. 7.

Figure 8:
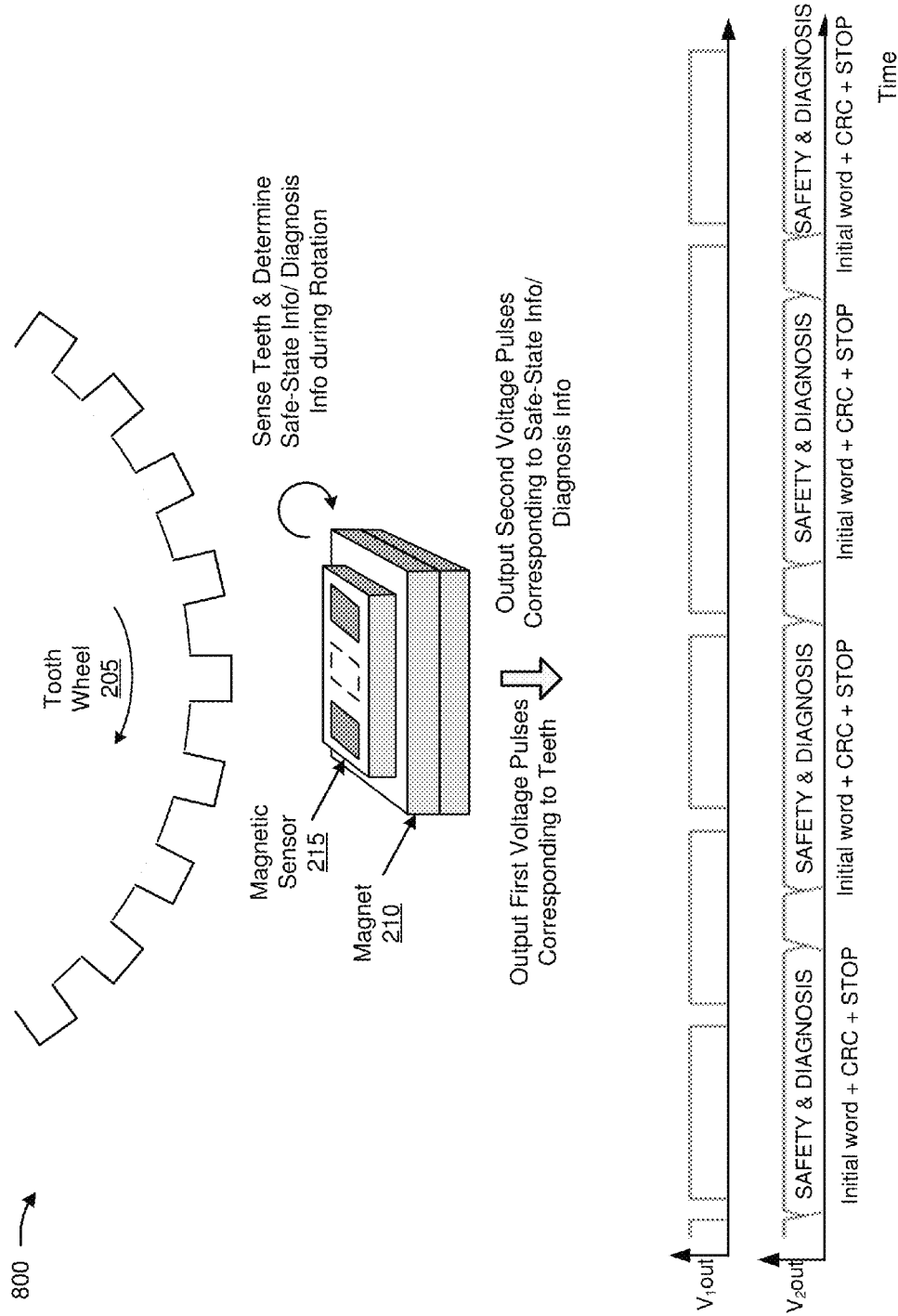
FIG. 8 is a diagram of an example implementation of a magnetic sensor that transmits profile information, associated with a magnet wheel, and safe-state information and/or diagnosis information, associated with the magnetic sensor and/or the magnet wheel, via a first output terminal and second output terminal, respectively.

FIG. 8 is a diagram of an example implementation 800 of magnetic sensor 215 that transmits profile information, associated with tooth wheel 205, and safe-state/diagnosis information, associated with magnetic sensor 215 and/or tooth wheel 205, via a first output terminal and a second output terminal, respectively. For the purposes of example implementation 800, assume that magnetic sensor 215 is positioned to sense a magnetic field, generated by magnet 210 and distorted by tooth wheel 205, and that tooth wheel 205 includes a set of teeth on a circumference of tooth wheel 205. Further, assume that magnetic sensor 215 is configured to output, to ECU 220 and during a rotation of the wheel, a signal that represents profile information of tooth wheel 205 (e.g., a signal that identifies each tooth as detected by magnetic sensor 215).

As shown in FIG. 8, tooth wheel 205 may rotate in a particular (e.g., clockwise) direction, and magnetic sensor 215 may sense the magnetic field produced by magnet 210 as distorted by tooth wheel 205. As shown, magnetic sensor 215 may determine, based on the magnetic field sensed during the rotation of tooth wheel 205, safe-state information and/or diagnosis information associated with magnetic sensor 215 and/or tooth wheel 205.

As further shown in FIG. 8, magnetic sensor 215 may transmit, during the rotation of tooth wheel 205, a signal that represents the profile of tooth wheel 205. For example, as shown, magnetic sensor 215 may transmit a first set of output voltages by modifying a signal, transmitted via a first output terminal of magnetic sensor 215, to output a 45 μs voltage pulse corresponding to each tooth of tooth wheel 205 (e.g., where each falling edge of the signal may identify an end of a tooth).

As further shown in FIG. 8, magnetic sensor 215 may also transmit a second set of output pulses that represents the safe-state/diagnosis information. For example, as shown by FIG. 8, magnetic sensor 215 may output a second set of voltage pulses, via a second output terminal, that represents the safe-state/diagnosis information. Here, magnetic sensor 215 may output, via the second output terminal, a second set of voltage pulses that represents an initial word, a CRC word, a sequence of bits of the safe-state/diagnosis information, and a stop word. Magnetic sensor 215 may then output, via the second output terminal, additional sets of voltage pulses that represent additional bits of the safe-state/diagnosis information. As shown, magnetic sensor 215 may output the second set of voltage pulses at any time during and/or after the rotation of tooth wheel 205 since the second set of voltage pulses is provided via a different output terminal than the first set of voltage pulses (i.e., independent of the first set of voltage pulses). In this example, ECU 220 may be configured to receive the second set of voltage pulses, and determine the safe-state/diagnosis information based on interpreting the second set of voltage pulses in accordance with a voltage modulation scheme stored or accessible by ECU 220.

As indicated above, FIG. 8 is provided merely as an example. Other examples are possible and may differ from what was described with regard to FIG. 8.

Figure 9A:
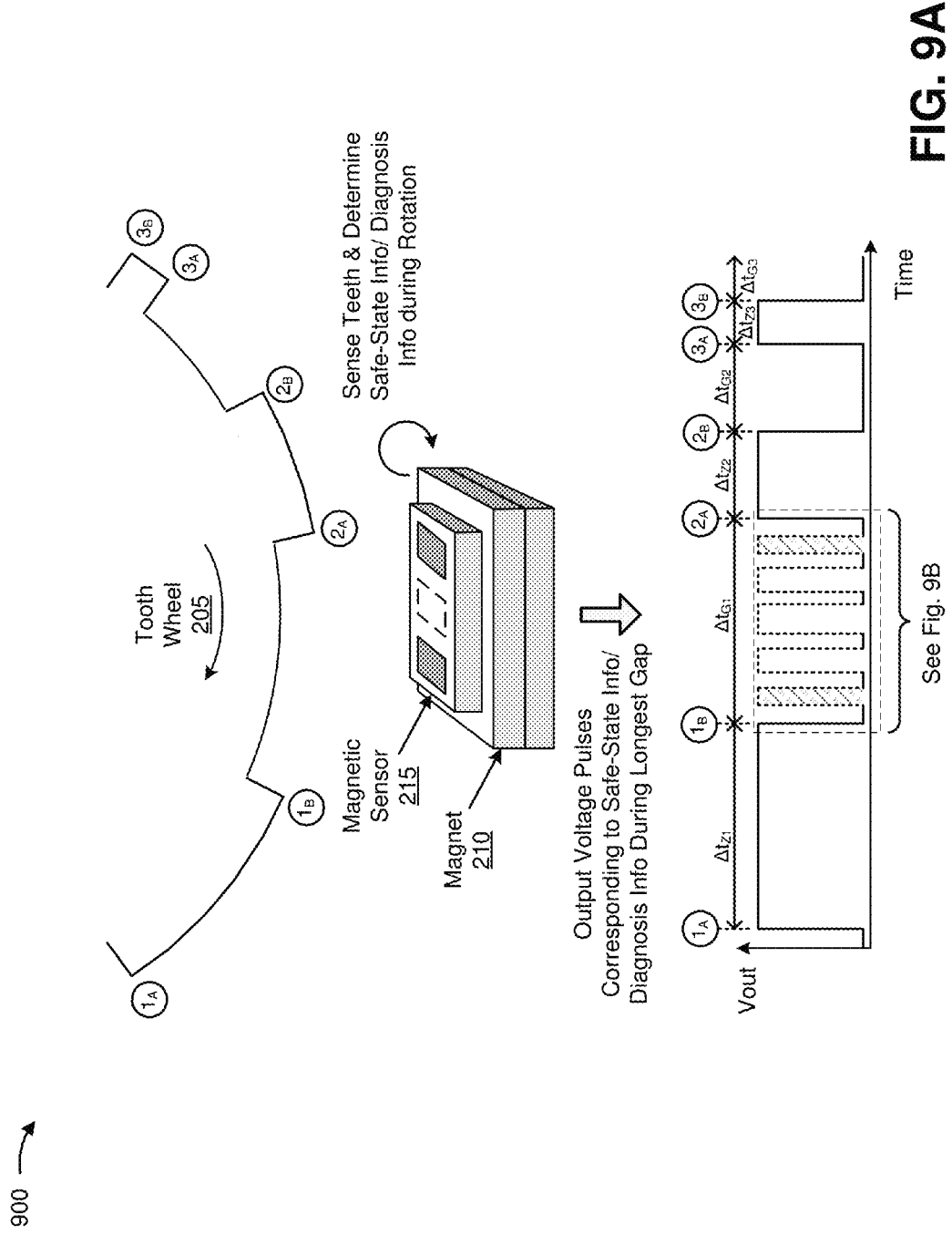
FIGS. 9A and 9B are diagrams of an example implementation of a magnetic sensor that transmits profile information, associated with a magnet wheel including varying tooth lengths and tooth gap widths, and safe-state information and/or diagnosis information, associated with the magnetic sensor and/or the magnet wheel.
Figure 9B:
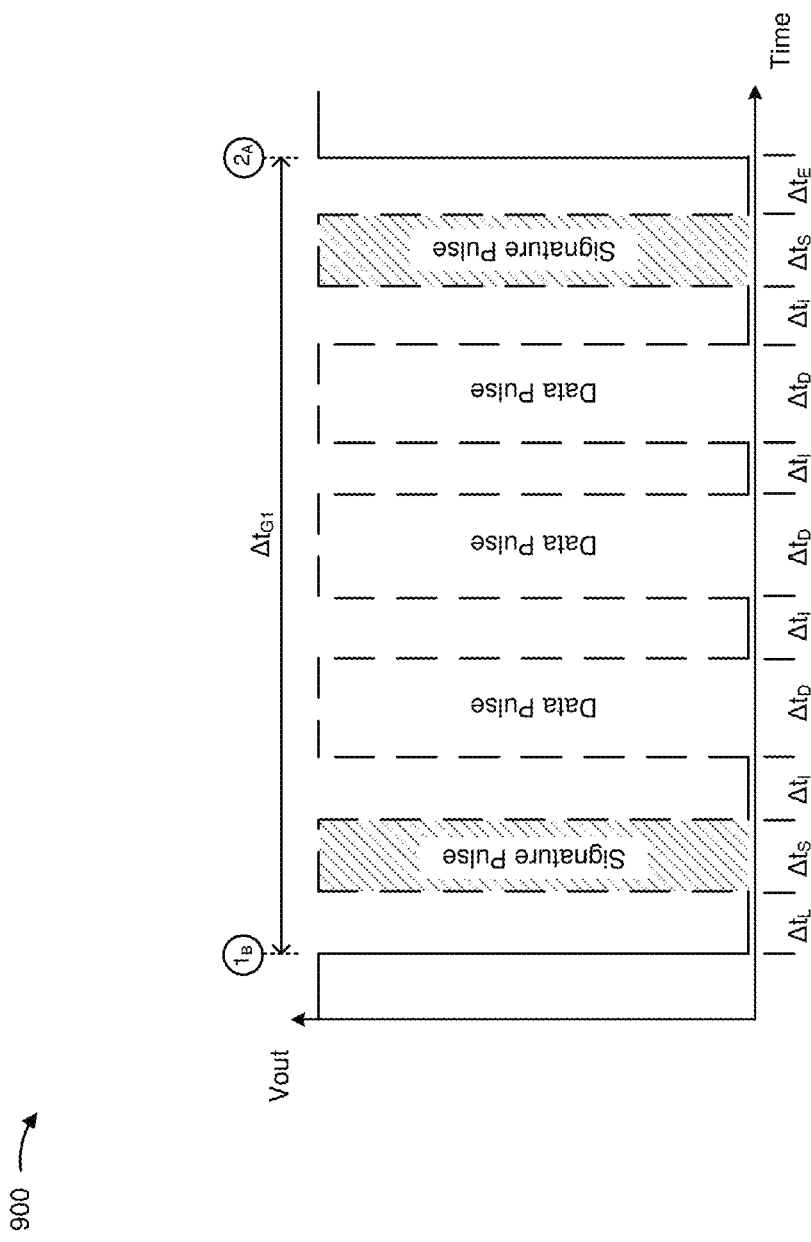

FIGS. 9A and 9B are diagrams of an example implementation 900 of magnetic sensor 215 that transmits profile information, associated with tooth wheel 205 having varying tooth lengths and tooth gap widths, and safe-state information and/or diagnosis information, associated with the magnetic sensor and/or tooth wheel 205. For the purposes of example implementation 900, assume that magnetic sensor 215 is positioned to sense a magnetic field, generated by magnet 210 and distorted by tooth wheel 205, and that tooth wheel 205 is an asymmetrical tooth wheel that includes a set of teeth of varying width and a set of tooth gaps of varying width on a circumference of tooth wheel 205. Further, assume that magnetic sensor 215 is configured to output, to ECU 220 and during a rotation of tooth wheel 205, a signal that represents profile information of tooth wheel 205 (e.g., a signal that identifies each tooth as detected by magnetic sensor 215).

As shown in FIG. 9A, tooth wheel 205 may rotate in a particular direction (e.g., clockwise), and magnetic sensor 215 may sense the magnetic field produced by magnet 210 and distorted by tooth wheel 205. As shown, magnetic sensor 215 may determine, based on the magnetic field sensed during the rotation of tooth wheel 205, profile information associated with tooth wheel 205 and safe-state information and/or diagnosis information associated with magnetic sensor 215 and/or tooth wheel 205.

As further shown in FIG. 9A, magnetic sensor 215 may transmit, during the rotation of tooth wheel 205, a signal that represents the profile of tooth wheel 205. For example, as shown, magnetic sensor 215 may modify a signal by outputting a voltage pulse that corresponds to each tooth of tooth wheel 205 (e.g., where each rising and falling edge of the signal may identify a leading and trailing edge of a tooth, respectively). For example, as shown, magnetic sensor 215 may output a first voltage pulse with a first pulse length (e.g., $\Delta t_{Z1}$) that corresponds to a first tooth (with a leading edge and a trailing edge identified as $1_A$ and $1_B$, respectively). As further shown, magnetic sensor 215 may output a second voltage pulse with a second pulse length (e.g., $\Delta t_{Z2}$) that corresponds to a second tooth (with a leading edge and a trailing edge identified as $2_A$ and $2_B$, respectively). As further shown, magnetic sensor 215 may output a third voltage pulse with a third pulse length (e.g., $\Delta t_{Z3}$) that corresponds a third tooth (with a leading edge and a trailing edge identified as $3_A$ and $3_B$, respectively).

For the purposes of example implementation 900, assume that magnetic sensor 215 identifies (e.g., based on multiple rotations of tooth wheel 205) that a tooth gap between the first tooth and the second tooth (e.g., corresponding to time $\Delta t_{G1}$) is a longer than a tooth gap between the second tooth and the third tooth (e.g., corresponding to time $\Delta t_{G2}$), a tooth gap between the third tooth and a fourth tooth (e.g., corresponding to time $\Delta t_{G3}$), and all other tooth gaps of tooth wheel 205. As such, magnetic sensor 215 may determine that magnetic sensor 215 is to transmit the safe-state/diagnosis information during time period $\Delta t_{G1}$ and, as shown in FIG. 9A, may transmit the safe-state/diagnosis information accordingly.

FIG. 9B includes a detailed view of the transmission of the safe-state/diagnosis information by magnetic sensor 215 during time period $\Delta t_{G1}$. As shown in FIG. 9B, when transmitting the safe-state diagnosis information, magnetic sensor 215 may transmit a sequence of voltage pulses that includes signature pulses and data pulses.

A signature pulse may include a pulse that indicates that magnetic sensor 215 is starting or stopping transmission of safe-state/diagnosis information. The signature pulses associated with example implementation 900 are identified as hatched areas in FIG. 9B, with signature pulse lengths of $\Delta t_S$. In some implementations, the signature pulse may be of a pulse length that is shorter than a pulse length associated with a narrowest tooth of tooth wheel 205 (e.g., such that ECU 220 does not treat the signature pulse as an indication of a tooth). For example, with respect to example implementation 900, the signature pulse length is less than the width of the third tooth such that $\Delta t_S < \Delta t_{Z3}$. As such, the signature pulse may ensure safe transmission of the safe-state/diagnosis information.

In some implementations, magnetic sensor 215 may transmit a first signature pulse to indicate that transmission of the safe-state/diagnosis information is to begin and, after transmitting the safe-state/diagnosis information via a set of data pulses, may transmit a second signature pulse to indicate that the transmission of the safe-state/diagnosis information is finished.

In some implementations, magnetic sensor 215 may transmit the first signature pulse after waiting for an amount of time after a trailing edge of a tooth (herein referred to as a loading time). For example, as shown in FIG. 9B, magnetic sensor 215 may wait for time $\Delta t_L$ after the trailing edge of the first tooth before transmitting the first signature pulse. Here, if ECU 220 stores or has access to information that identifies the loading time, then ECU 220 may be capable of determining whether information received at after the last tooth is a signature pulse or a pulse associated with profile information of tooth wheel 205. For example, if ECU 220 receives a pulse after an amount of time passes that is approximately equal to the loading time, then ECU may determine that the pulse is a signature pulse.

As further shown, after the first signature pulse, magnetic sensor may transmit one or more data pulses (e.g., of pulse length $\Delta t_D$ as shown in FIG. 9B). The one or more data pulses may include the safe-state/diagnosis information encoded in a manner similar to that described above. In some implementations, magnetic sensor 215 may transmit one or more data pulses. Additionally, or alternatively, the one or more data pulses may have a same pulse length or different pulse lengths. In some implementations, a pulse length of a data pulse may be longer than the pulse length associated with the narrowest tooth of tooth wheel 205 (e.g., since magnetic sensor 220 has already indicated that magnetic sensor 215 is transmitting the safe-state/diagnosis information via the first signature pulse, ECU 220 will not interpret the data pulse as profile information). Alternatively, the pulse length of a data pulse may be shorter than the pulse length associated with the narrowest tooth of tooth wheel 205 (e.g., when magnetic sensor 220 does not transmit the signature pulse before transmitting the safe-state/diagnosis information). In some implementations, magnetic sensor 215 may be configured to wait for an amount of time after transmitting a data pulse and/or a signature pulse before transmitting an additional output pulse (e.g., identified as $\Delta t_I$ in FIG. 9B).

As further shown in FIG. 9B, magnetic sensor 215 may transmit a second signature pulse after transmitting the safe-state/diagnosis information. As shown, magnetic sensor 215 may transmit the second signature pulse such that a particular amount of time remains before magnetic sensor 215 senses a leading edge of a next tooth of tooth wheel 205. In this way, magnetic sensor 215 may safely transmit profile information and safe-state/diagnosis information for an asymmetrical tooth wheel 205.

In some implementations, magnetic sensor 230 may transmit a signature pulse to indicate that transmission of the safe-state/diagnosis information is to begin, and may not transmit another signature pulse. In such a case, ECU 220 may be configured to determine that the transmission of the safe-state/diagnosis information ends when, for example, a particular amount of time lapses after the signature pulse is received. Here, ECU 220 may be configured to identify pulses received during the particular amount of time as pulses that include the safe-state diagnosis information.

In some implementations, magnetic sensor 230 may not transmit any signature pulse before transmitting the safe-state/diagnosis information. In such a case, magnetic sensor 230 may be configured to wait, after a trailing edge of a tooth, for the loading time to lapse before transmitting the safe-state/diagnosis information. Here, ECU 220 may store or have access to information that identifies the loading time such that ECU 220, when receiving a pulse after an amount of time that is approximately equal to the loading time (e.g., after the previous pulse associated with a tooth), identifies the pulse as including safe-state/diagnosis information.

As indicated above, FIGS. 9A and 9B are provided merely as examples. Other examples are possible and may differ from what was described with regard to FIGS. 9A and 9B.

Implementations described herein may allow a magnetic sensor to transmit safe-state information and/or diagnosis information, associated with a possible fault and/or an operational state, without compromising an ability of the magnetic sensor to transmit profile information associated with a magnet wheel. For example, implementations described herein may allow the magnetic sensor to transmit the safe-state information and/or the diagnosis information by transmitting one or more voltage pulses (e.g., during a time period corresponding to a reference zone associated with the magnet wheel, during time periods corresponding to one or more tooth gaps associated with the magnet wheel, at another time during the rotation of the magnet wheel, etc.) and/or by outputting one or more current pulses during the rotation of the magnet wheel.

The foregoing disclosure provides illustration and description, but is not intended to be exhaustive or to limit the implementations to the precise form disclosed. Modifications and variations are possible in light of the above disclosure or may be acquired from practice of the implementations.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A magnetic sensor, comprising:
one or more components configured to:
sense a magnetic field during a rotation of a wheel,
the sensed magnetic field representing a profile of the wheel during the rotation;
detect, based on the sensed magnetic field, a possible fault of at least one of the magnetic sensor or the wheel;
transmit, to a control unit, a first set of output pulses corresponding to the profile of the wheel during the rotation,
the first set of output pulses being transmitted during the rotation of the wheel; and
transmit, to the control unit, a second set of output pulses that indicates the magnetic sensor detected the possible fault.

2. The magnetic sensor of claim 1, where the first set of output pulses includes a first set of voltage pulses and the second set of output pulses includes a second set of voltage pulses,
the second set of voltage pulses being provided during a time period corresponding to a particular section of the wheel, and
the second set of voltage pulses and the first set of voltage pulses being provided via a same voltage interface of the magnetic sensor.

3. The magnetic sensor of claim 1, where the first set of output pulses includes a first set of voltage pulses and the second set of output pulses includes a second set of voltage pulses,
the second set of voltage pulses being provided during a set of time periods corresponding to at least one reference zone gap associated with the wheel,
the at least one reference zone gap having a width wider than a tooth gap width between teeth of the wheel, and
the second set of voltage pulses being provided between voltage pulses of the first set of voltage pulses,
the second set of voltage pulses and the first set of voltage pulses being provided via a same voltage interface of the magnetic sensor.

4. The magnetic sensor of claim 1, where the first set of output pulses includes a set of voltage pulses and the second set of output pulses includes a set of current pulses.

5. The magnetic sensor of claim 1, where the first set of output pulses includes a first set of voltage pulses and the second set of output pulses includes a second set of voltage pulses,
the second set of voltage pulses being provided via a first output terminal of the magnetic sensor,
the first set of voltage pulses being provided via a second output terminal of the magnetic sensor,
the first output terminal being different from the second output terminal.

6. The magnetic sensor of claim 1, where, in operation of the magnetic sensor, the wheel is associated with a crankshaft or a camshaft of a motor vehicle.

7. The magnetic sensor of claim 1, where the first set of output pulses is output during a time period that is complementary to a time period during which the second set of output pulses is output,
the first set of output pulses and the second set of output pulses representing a full rotation of the wheel.

8. A magnetic sensor, comprising:
one or more sensor components configured to:
sense, during a rotation of a wheel, a magnetic field that corresponds to profile information associated with the wheel;
detect, based on the sensed magnetic field, an operational state of at least one of the magnetic sensor or the wheel,
the operational state being a possible fault of at least one of the magnetic sensor or the wheel;
output, to a control unit and during the rotation of the wheel, a first set of output pulses that represents the profile information associated with the wheel; and
output, to the control unit a second set of output pulses that indicates that the magnetic sensor detected the operational state.

9. The magnetic sensor of claim 8, where the first set of output pulses includes a first set of voltage pulses and the second set of output pulses includes a second set of voltage pulses,
the second set of voltage pulses being provided during a time period corresponding to at least one reference zone gap of the wheel,
the at least one reference zone gap having a width wider than a tooth gap width between teeth of the wheel, and
the second set of voltage pulses being provided between voltage pulses of the first set of voltage pulses,
the second set of voltage pulses and the first set of voltage pulses being provided via a same voltage interface of the magnetic sensor.

10. The magnetic sensor of claim 8, where the first set of output pulses includes a first set of current pulses and the second set of output pulses includes a second set of current pulses,
the first set of current pulses and the second set of current pulses being provided via an output terminal of the magnetic sensor.

11. The magnetic sensor of claim 8, where the operational state of the magnetic sensor or the wheel is associated with information including at least one bit of safe-state information or diagnosis information associated with the magnetic sensor or the wheel.

12. The magnetic sensor of claim 8, where the one or more sensor components include at least one of:

a Hall-based sensing element;

a giant magnetoresistance (GMR)-based sensing element;

an anisotropic magnetoresistance (AMR)-based sensing element;

a tunnel magnetoresistance (TMR)-based sensing element; or a variable reluctance (VR)-based sensing element.

13. The magnetic sensor of claim 8, where the first set of output pulses and the second set of output pulses represent a full rotation of the wheel.

14. The magnetic sensor of claim 8, where the first set of output pulses is output at a time when the second set of output pulses is not being output.

15. A method, comprising:

sensing, by a magnetic sensor, a magnetic field during a rotation of a wheel, the sensed magnetic field corresponding to a profile of the wheel during the rotation;

detecting, by the magnetic sensor and based on the sensed magnetic field, a possible fault of the magnetic sensor or the wheel;

providing, by the magnetic sensor and during the rotation of the wheel, a first set of output pulses associated with the profile of the wheel to a control unit; and providing, to the control unit and by the magnetic sensor, a second set of output pulses that indicates that the magnetic sensor detected the possible fault.

16. The method of claim 15, where the first set of output pulses includes a first set of voltage pulses and the second set of output pulses includes a second set of voltage pulses, the second set of voltage pulses being provided during a set of time periods corresponding to at least one reference zone gap associated with the wheel, the at least one reference zone gap having a width wider than a tooth gap width between teeth of the wheel, and the second set of voltage pulses and the first set of voltage pulses being provided via a same transmission interface of the magnetic sensor.

17. The method of claim 15, where the wheel includes a plurality of teeth, and where each output pulse, of the first set of output pulses, includes a rising edge or a falling edge corresponding to a tooth of the plurality of teeth of the wheel.

18. The method of claim 15, where the wheel includes a plurality of teeth, and where each output pulse, of the first set of output pulses, includes a rising edge corresponding to a first edge of a tooth, of the plurality of teeth of the wheel, and a falling edge corresponding to a second edge of the tooth.

19. The method of claim 15, where the second set of output pulses includes at least one signature pulse, the at least one signature pulse having a pulse length that is shorter than a shortest output pulse of the first set of output pulses.

20. The method of claim 15, where providing the second set of output pulses comprises:

waiting for a loading time to lapse after outputting a particular pulse of the first set of output pulses; and providing the second set of output pulses when the loading time has lapsed, the second set of output pulses including zero signature pulses, one signature pulse, or two signature pulses.

* * * * *